(12) United States Patent
Kato et al.

(10) Patent No.: US 7,487,683 B2
(45) Date of Patent: Feb. 10, 2009

(54) ENDURANCE TESTING APPARATUS

(75) Inventors: Masaaki Kato, Kariya (JP); Maiko Futamura, Obu (JP); Hiroshi Miyagawa, Yokohama (JP)

(73) Assignees: Denso Corporation, Kariya (JP); Toyota Tsusho Corporation, Nagoya (JP)

( * ) Notice: Subject to any disclaimer, the term of this patent is extended or adjusted under 35 U.S.C. 154(b) by 28 days.

(21) Appl. No.: 11/392,867

(22) Filed: Mar. 30, 2006

(65) Prior Publication Data

US 2006/0219024 A1    Oct. 5, 2006

(30) Foreign Application Priority Data

Mar. 31, 2005  (JP)  ............................. 2005-102863
Jan. 20, 2006  (JP)  ............................. 2006-012703

(51) Int. Cl.
  *G01B 7/16*  (2006.01)
  *G01L 1/00*  (2006.01)
(52) U.S. Cl. ....................................... 73/766
(58) Field of Classification Search ................. 73/766
  See application file for complete search history.

(56) References Cited

U.S. PATENT DOCUMENTS 4,102,180 A * 7/1978 Devarakonda et al. ........ 73/794
5,156,341 A * 10/1992 Terakado et al. .......... 239/585.4
5,625,154 A * 4/1997 Matsuhiro et al. ............. 73/774
5,970,614 A * 10/1999 Adachi et al. ............. 29/888.44
6,546,782 B1 * 4/2003 De La Cruz et al. ............. 73/7
6,752,001 B1 * 6/2004 LaPointe ....................... 73/10

FOREIGN PATENT DOCUMENTS

| JP | 7-63748 | 3/1995 |
| JP | 11-281531 | 10/1999 |

* cited by examiner

*Primary Examiner*—Edward Lefkowitz
*Assistant Examiner*—Octavia Davis
(74) *Attorney, Agent, or Firm*—Nixon & Vanderhye PC

(57) ABSTRACT

An endurance testing apparatus, which is for performing an endurance test of a contacting/separating portion in which a first member and a second member repeats contacting with and separating from each other, has a contact load generator and a testing medium fluid supply means. The contact load generator reciprocates the second member relative to the first member to generate a contact load acting between the first member and the second member repeatedly. The testing medium fluid supply means supplies a testing medium fluid to the contacting/separating portion to expose the first member and the second member to the testing medium fluid.

18 Claims, 13 Drawing Sheets

ENDURANCE TESTING APPARATUS

CROSS REFERENCE TO RELATED APPLICATION

This application is based upon and claims the benefit of priority of Japanese Patent Applications No. 2005-102863 filed on Mar. 31, 2005 and No. 2006-012703 filed on Jan. 20, 2006, the contents of which are incorporated herein by reference.

FIELD OF THE INVENTION

The present invention relates to an endurance testing apparatus for evaluating endurance of a mechanical device, especially to the endurance testing apparatus for performing an endurance test of a contacting/separating portion in which a first member and a second member of the mechanical device repeats contacting with and separating from each other in a testing medium fluid.

BACKGROUND OF THE INVENTION

High frequency reciprocating rig (HFRR), which is schematically shown in FIG. 15, is known as a general endurance testing apparatus. The high frequency reciprocating rig reciprocates a test specimen ball J1 at high frequency in pushing the test specimen ball J1 onto a test specimen plate J2 at constant load, in a condition that the test specimen ball J1 and the test specimen plate J2 are exposed to testing medium fluid such as oil, fuel, etc. The endurance of the test specimen is evaluated by using the abrasion amount on the test specimen plate J2.

The high frequency reciprocating rig can perform the endurance test in a simple fashion. However, high frequency reciprocating rig has a construction to slide the two members J1, J2 on each other in pushing them onto each other. Thus, the high frequency reciprocating rig is not suitable for the endurance test of the test specimen such as a fuel injection valve, in which a first member and a second member such as a nozzle body and a needle of a fuel injection valve repeats contacting with and separating from each other.

The high frequency reciprocating rig further has the following issues. Firstly, the testing medium fluid J3 is received in the opened vessel J4, so that the abrasion power tends to be accumulated at the sliding portion of the two members J1, J2. The abrasion powder can vary the abrasion amount. Next, the testing medium fluid J3 is received in the opened vessel J4, so that it is not possible to perform the endurance test in a case that the testing medium fluid J3 is volatile ones such as low critical fuel, gaseous fuel, etc. Further, the testing medium fluid J3 is received in the opened vessel J4, so that it is difficult to control the temperature of the testing medium fluid J3 with accuracy. The temperature of the testing medium fluid J3 affects the abrasion amount, so that the accuracy of the endurance test is spoiled. Furthermore, the surface pressure on the contact portion gradually decreases in accordance with the progress of the abrasion of the two members J1, J2, so that the result of the endurance test tends to vary. Still further, the lubrication performance at the sliding portion of the two members J1, J2 is evaluated by the abrasion amount, however, the abrasion amount is too varied to evaluate the lubrication performance, except the condition that the abrasion amount is quite small or quite large.

As described above, the high frequency reciprocating rig is not suitable for the endurance test of the test specimen such as a fuel injection valve, in which the first member and the second member repeats contacting with and separating from each other. In view of the issues of the high frequency reciprocating rig, JP-H11-281531-A and JP-H07-063748-A, for example disclose endurance testing apparatuses for evaluating the abrasion amount of respective portions of an internal combustion engine that performs the endurance test by driving the internal combustion engine by using an electric motor. However, the endurance testing apparatuses disclosed in JP-H11-281531-A and JP-H07-063748-A have the following issues.

Firstly, the endurance testing apparatus incorporates an actual internal combustion engine. This increases the size and cost of the endurance testing apparatus, and it is difficult to perform a large number of endurance tests by this endurance testing apparatus. Next, the rotational speed, i.e., the number of revolutions per unit time of the internal combustion engine, is limited. This extends the time necessary for the endurance test, and it is not possible to perform the endurance test in a short time. Further, the internal combustion engine is driven by the electric motor, and no fuel is supplied to the fuel injection system. Accordingly, it is not possible to evaluate the reliability of the fuel injection system by this endurance testing apparatus. The evaluation of the abrasion amount of the fuel injection system is generally performed by injecting the fuel out of the fuel injection system, however, the driving device is large and the rotational speed is limited as mentioned above.

As described above, (1) high frequency reciprocating rig can perform the endurance test in a simple fashion, but is not suitable for the test specimen such as a fuel injection valve, in which the first member and the second member repeats contacting with and separating from each other. (2) The endurance testing apparatus disclosed in JP-H11-281531-A or JP-H07-063748-A incorporates an actual internal combustion engine. This increases the cost for performing the endurance test. The rotational speed of the internal combustion engine is limited, so that it is not possible to perform the endurance test in a short time.

SUMMARY OF THE INVENTION

The present invention is achieved in view of the above-described issues, and has an object to provide an endurance testing apparatus that is suitable for performing an endurance test of a test specimen a first member and a second member of which repeat contacting with and separating from each other, and to decrease the time and the cost for performing the endurance test.

The endurance testing apparatus, which is for performing an endurance test of a contacting/separating portion in which a first member and a second member repeats contacting with and separating from each other, has a contact load generator and a testing medium fluid supply means. The contact load generator reciprocates the second member relative to the first member to generate a contact load acting between the first member and the second member repeatedly. The testing medium fluid supply means supplies a testing medium fluid to the contacting/separating portion to expose the first member and the second member to the testing medium fluid.

BRIEF DESCRIPTION OF THE DRAWINGS

Features and advantages of embodiments will be appreciated, as well as methods of operation and the function of the related parts, from a study of the following detailed description, the appended claims, and the drawings, all of which form a part of this application. In the drawings:

DETAILED DESCRIPTION OF PREFERRED EMBODIMENTS

First Embodiment

An endurance testing apparatus according to the first embodiment is described in the following, referring to FIGS. 1 to 10.

The endurance testing apparatuses in the first to fourth embodiments are for performing an endurance test of a nozzle assembly in a fuel injection valve. The fuel injection valve is an example of a test specimen in which a first member and a second member repeatedly come in contact with and apart from each other. In the first to third embodiments, the endurance testing apparatuses performs the endurance test adopt by using low critical fuel such as alcohol fuel, which is easily vaporized at normal temperature and normal pressure.

Firstly, the nozzle assembly, of which the endurance is tested by the endurance testing apparatus, is described in the following.

The nozzle assembly is for starting and stopping fuel injection in the fuel injection valve, which injects fuel in an internal combustion engine, and formed from a nozzle body 1 and a needle 2. The nozzle body 1 is an example of a valve body, and corresponds to the first member according to the present invention. The needle 2 is an example of a valve element, and corresponds to the second member according to the present invention.

In a state that the fuel injection valve is mounted on an internal combustion engine, the needle 2 reciprocatingly moves with respect to the nozzle body 1 in the nozzle assembly, so that the nozzle body 1 and the needle 2 repeats contacting with and separating from each other. Specifically, a seat portion of the needle 2 repeats seating on and lifting off a valve seat of the nozzle body 1, for example.

In the following, a portion of the valve seat of the nozzle body 1 and a portion of seat portion of the needle 2, which repeat contacting with and separating from each other, are referred to as a contacting/separating portion A.

An example of the nozzle assembly is described in the following.

Figure 1:
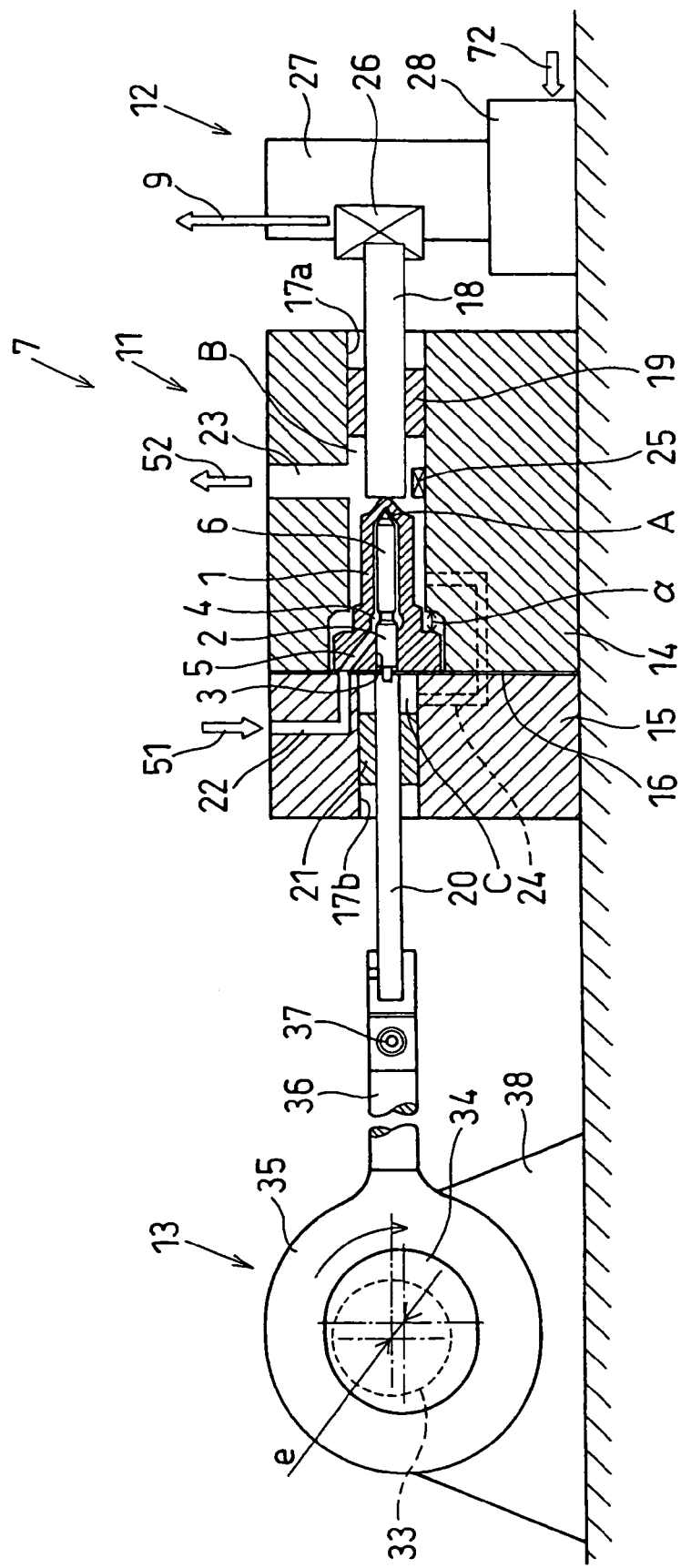
FIG. 1 is a schematic cross-sectional view showing a principal portion of an endurance testing apparatus according to a first embodiment of the present invention.

The nozzle body 1 has one injection hole or more at its right leading end portion in FIG. 1. The nozzle body 1 has a sliding bore 3 therein, which slidably supports a rod-shaped needle 2. An inner circumference of the sliding bore 3 is extended radially outward at its longitudinal middle portion, to provide an oil accumulator 4. The nozzle body 1 has a fuel supply passage 5 therein to supply fuel from an outside to the oil accumulator 4.

The needle 2 is rod-shaped member that is slidably supported in the sliding bore 3 of the nozzle body 1. The seat portion, which is provided at a leading end of the needle 2, is seated on and lifted off the valve seat, which is formed at the leading end side in the nozzle body 1, to close and open the injection hole. The needle 2 is provided with a small diameter portion 6, which extends from a proximity to the oil accumulator 4 to the seat portion and has a diameter smaller than that of the sliding bore 3. The fuel passage, which is formed between the small diameter portion 6 and the sliding bore 3, supplies the fuel from the oil accumulator 4 to the leading end side of the nozzle body 1. That is, the fuel, which is led from the outside to the oil accumulator 4 via the fuel supply passage 5, is further supplied to contacting/separating portion A via the fuel passage between the small diameter portion 6 and the sliding bore 3.

The nozzle assembly has a construction as described above, so that an inner space of the nozzle body 1 is communicated with the injection hole when the seat portion of the needle 2 is lifted off the valve seat of the nozzle body 1, to start injecting the fuel, which is supplied from the fuel supply passage 5 to the nozzle body 1, out of the injection hole. When the seat portion of the needle 2 is seated on the valve seat of the nozzle body 1, the communication between the inner space of the nozzle body 1 and the injection hole is interrupted, to stop fuel injection.

The endurance testing apparatus repeats contacting and separating operations between the nozzle body 1 and the needle 2 in a condition that the contacting/separating portion A is exposed to the fuel. The endurance testing apparatus includes a testing apparatus body 7, a fuel circulation system 8 and a control unit 9. The testing apparatus body 7 has a function to generate a contact load between the nozzle body 1 and the needle 2. That is, the testing apparatus body 7 reciprocatingly moves the needle 2 with respect to the nozzle needle 1 so that the nozzle body 1 and the needle 2 repeat contacting with and separating from each other. The fuel circulation system 8 is an example of a testing medium fluid supply means according to the present invention, and supplies the fuel to the contacting/separating portion A of the testing the nozzle body 1 and the needle 2. The control unit 9 commands an operation control of the endurance testing apparatus.

The testing apparatus body 7 includes a body block 11 that installs the nozzle assembly therein, a contact load adjuster 12 that adjusts the contact load between the nozzle body 1 and the needle 2 and the contact load generator 13 that moves the needle 2 reciprocatingly so that the nozzle body 1 and the needle 2 repeats contacting with and separating from each other.

The body block 11 is described in the following, referring to FIG. 1.

The body block 11 includes a first block 14 and a second block 15. The nozzle assembly is installed in the first block 14, and then the first block 14 is connected to the second block 15, to operate the endurance testing apparatus. The first block 14 and the second block 15 sandwiches a first seal member 16 therebetween, to prevent the fuel filled in a space, which installs the nozzle assembly therein and is referred to as a nozzle installation space B in the following, from leaking outward.

The first block 14 and the second block 15 are respectively provided with through holes 17a, 17b to be coaxial with each other.

A load shaft 18 is inserted in the through hole 17a of the first block 14. The load shaft 18 takes out the contact load between the nozzle body 1 and the needle 2. A second seal member 19 is interposed between an inner circumference of the through hole 17a of the first block 14 and an outer circumference of the load shaft 18, to support the load shaft 18 to be slidable in its axial direction and to prevent the fuel filled in the nozzle installation space B from leaking outward.

A drive shaft 20 is inserted in the through hole 17b of the second block 15. The drive shaft 20 moves the needle 2, which is installed in the nozzle body 1, reciprocatingly in its axial direction. A third seal member 21 is interposed between an inner circumference of the through hole 17b of the second block 15 and an outer circumference of the drive shaft 20, to support the drive shaft to be slidable in its axial direction and to prevent the fuel filled in the nozzle pressure release chamber C from leaking outward.

The nozzle assembly is placed in the nozzle installation space B, which is provided between the load shaft 18 and the drive shaft 20 in their axial direction in the through hole 17a of the first block 14. The needle 2 is connected to a leading end of the drive shaft 20, to support the nozzle assembly to align a center axis of the nozzle body 1 with those of the load shaft 18 and the drive shaft 20. In this manner, the nozzle body 1 is supported in a radial direction in the body block 11, keeping a state that an outer circumferential face of the nozzle body 1 does not come in contact with the body block 11.

A construction to support the nozzle body 1 in the axial direction is described in the following. The load shaft 18 pushes the nozzle body 1 toward the second block 15. A pushing load for the load shaft 18 to push the nozzle body 1 toward the second block 15, which is associated with the contact load, is described below. As shown in FIG. 1, a face of the nozzle body 1, which is opposite from the second block 15, and an inner face of the nozzle installation space B in the first block 14 provides an axial clearance, therebetween. Thus, the contact load between the nozzle body 1 and the needle 2 is totally transmitted to the load shaft 18.

The fuel passage, which is formed in the body block 11, is described in the following.

The second block 15 has a fuel supply passage 22 to lead the fuel, which is supplied from an outside, i.e., from a second main passage 51 of the fuel circulation system 8, to the fuel supply passage 5 of the nozzle body 1.

The first block 14 has a fuel discharge passage 23 to discharge the fuel, which is injected out of the injection hole, to an outside, i.e., a third main passage 52 of the fuel circulation system 8.

In each of the first and second blocks 14, 15 is formed a communication passage 24 to communicate the nozzle installation space B in the first block 14 with the nozzle pressure release chamber C in the second block 15. The communication passage 24 leads the fuel, which is leaked into the nozzle pressure release chamber C through the clearance between the sliding bore 3 and the needle 2, to the nozzle installation space B.

In the nozzle installation space B, a first temperature sensor 25 is installed in a proximity to the injection hole, to detect fuel temperature of the fuel passed through the contacting/separating portion A. The first temperature sensor 25 outputs the fuel temperature to the control unit 9.

The testing apparatus body 7 has a contact load adjuster 12 to adjust the contact load between the nozzle body 1 and the needle 2.

The contact load adjuster 12 adjusts a position for the load shaft 18 to support an end portion of the nozzle body 1. The contact load adjuster 12 includes a load sensor 26, a sensor support block 27 that supports the load shaft 18 at a specific axial position via the load sensor 26, and an adjusting device 28 that moves the sensor support block 27 in the axial direction.

The load sensor 26, which is interposed between the load shaft 18 and the sensor support block 27, detects the contact load between the nozzle body 1 and the needle 2, which is transmitted via the load shaft 18. The load sensor 26 outputs the contact load to the control unit 9.

The control unit 9 controls the adjusting device 28 to move the sensor support block 27 based on the contact load detected by the load sensor 26. The control of the movement of the adjusting device 28, i.e., the control of the contact load between the nozzle body 1 and the needle 2 is further described below in detail.

Figure 2:
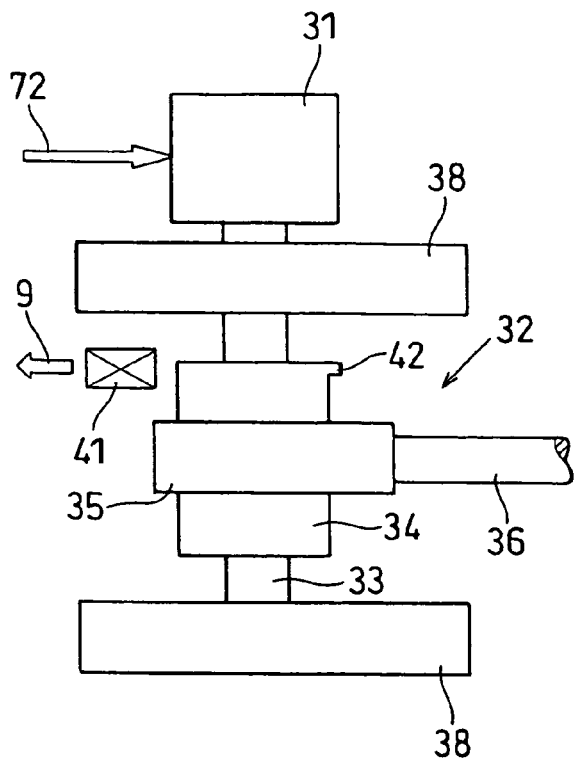
FIG. 2 is a top view showing a contact load generator of the endurance testing apparatus according to the first embodiment.

The contact load generator 13 is described in the following, referring to FIGS. 1 and 2.

The contact load generator 13 converts rotation into reciprocation. The contact load includes an electric motor 31 that generates rotational force and a rotation-reciprocation converter 32 that converts the rotation generated by the electric motor 31 into the reciprocation. The reciprocation, which is converted from the rotation by the rotation-reciprocation converter 32, is transmitted to the drive shaft 20, to reciprocate the needle, which is connected to the drive shaft 20.

The electric motor 31 is a conventional one that generates rotational force when it is energized. The control unit 9 controls the rotational speed and the rotational number of the electric motor 31, i.e., a contacting/separating speed and the contact repetition times.

The rotation-reciprocation converter 32 converts the rotation, which is generated by the electric motor 31, into the reciprocation. The rotation-reciprocation converter 32 includes a rotation shaft 33 that rotates integrally with the output shaft of the electric motor 31, an eccentric cam 34 that is fixed to the rotation shaft 33 and rotates eccentrically with respect to the rotation shaft 33, a driving ring 35 that is fitted to an outer circumferential face of the eccentric cam 34 to be rotationally slidable against the eccentric cam 34, a driving arm 36 that connects the driving ring 35 with the drive shaft 20, and a joint 37 that allows a shaking of the driving arm 36 and transmits only an axial displacement of the driving arm 36 to the drive shaft 20.

The rotation shaft 33 is rotatably supported by a shaft supporting member 38. The eccentric cam 34 has an outer circumference with a perfectly circular shape. A center of the outer circumference of the eccentric cam 34 is displaced from a rotational center of the rotation shaft 33. In FIG. 1, the referential sign "e" denotes a deviation of the center of an outer circumference of the eccentric cam 34 and the rotational center of the rotation shaft 33.

The contact load generator 13 is provided with a rotation sensor 41 to count the contact repetition times between the nozzle body 1 and the needle 2. The rotation sensor 41 detects a rotational state, i.e., a rotational speed and a rotational frequency of the rotation shaft 33. Specifically, in the first embodiment, the rotation sensor 41 is a pickup sensor that detects the rotation of the eccentric cam 34. The rotation sensor 41 detects the rotational state of the rotation shaft 33 by the first pulser 42, which is a magnetic body provided in the eccentric cam 34, coming closer to and away from the rotation sensor 41. The rotation sensor 41 outputs the rotational state of the rotation shaft 33 to the control unit 9.

Figure 3:
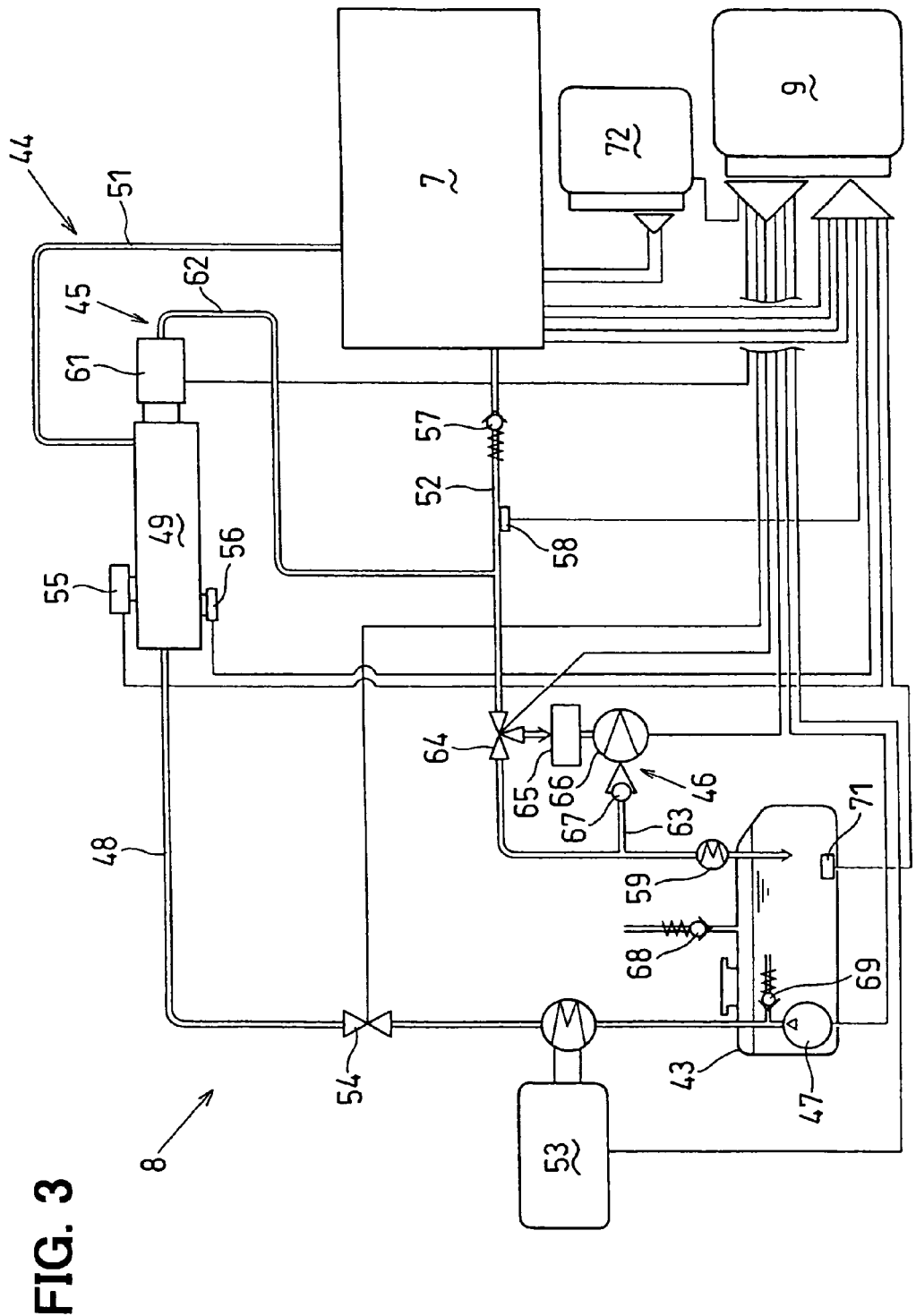
FIG. 3 is a block diagram schematically showing a construction of the endurance testing apparatus according to the first embodiment.

The fuel circulation system 8 is described in the following, referring to FIG. 3.

The fuel circulation system 8 forms a closed loop that supplies the fuel in the high-pressure fuel tank 43 to the testing apparatus body 7, collects the fuel passed through the testing apparatus body 7 in the high-pressure fuel tank 43, and supplies the collected fuel again to the testing apparatus body 7.

That is, the fuel circulation system 8 forms the closed loop, which supplies the fuel to be passed through the contacting/separating portion A between the nozzle body 1 and the needle 2 to the testing apparatus body 7, collects the fuel passed through the contacting/separating portion A between the nozzle body 1 and the needle 2, and supplies the collected fuel again to the contacting/separating portion A between the nozzle body 1 and the needle 2.

In the first embodiment, the fuel circulation system 8 includes a main circulation circuit 44, a body detour circuit 45 and a pressure return circuit 46. The circulation circuit 44 supplies the fuel in the high-pressure fuel tank 43 the testing apparatus body 7 and returns the fuel injected by the nozzle assembly body 7 again to the high-pressure fuel tank 43. The body detour circuit 45 returns the fuel to the high-pressure fuel tank 43 to detour the testing apparatus body 7. The pressure return circuit 46 pressurizes the fuel and then returns the fuel to the high-pressure fuel tank 43.

The main circulation circuit 44 is formed from a fuel circulation passage that returns the fuel in the high-pressure fuel tank 43 via a high-pressure pump 47, a first main passage 48, an accumulator 49, a second main passage 51, the testing apparatus body 7 and third main passage 52 to the high-pressure fuel tank 43.

The high-pressure pump 47 is a fuel pump, which pressurizes the fuel in the high-pressure fuel tank 43 at high pressure and pressure-feeds the fuel to the first main passage 48. The control unit 9 controls an operation of the high-pressure pump 47.

The first main passage 48 is a fuel pipe, which leads the fuel pressure-fed by the high-pressure pump 47, to the accumulator 49. A temperature adjusting device 53 and a cutoff valve 54 are installed on the way of the first main passage 48. The temperature adjusting device 53 adjusts the fuel temperature passing through the first main passage 48. The cutoff valve 54 opens and closes the first main passage 48.

Specifically, the temperature adjusting device 53 heats or cools the fuel passing through the first main passage 48. The control unit 9 controls an operation of the temperature adjusting device 53, to control the fuel temperature of the fuel passing through the first main passage 48.

The control unit 9 also controls opening and closing operations of the cutoff valve 54. The control unit 9 opens the cutoff valve 54 in the endurance testing operation, and closes the cutoff valve 54 when the endurance test stops.

The accumulator 49 is a fuel accumulating container that accumulates the fuel pressure-fed via the first main passage 48.

A first pressure sensor 55 is provided in the accumulator 49 to detect the fuel pressure in the accumulator 49. The first pressure sensor 55 detects the fuel pressure of the fuel to be supplied to the testing apparatus body 7, i.e., an injection pressure of the nozzle assembly. The first pressure sensor 55 outputs the fuel pressure in the accumulator 49 to the control unit 9.

A second temperature sensor 56 is also provided in the accumulator 49 to detect the fuel temperature in the accumulator 49. The second temperature sensor 56 detects the fuel temperature of the fuel to be supplied to the testing apparatus body 7, i.e., an injection temperature of the nozzle assembly. The second temperature sensor 56 outputs the fuel temperature in the accumulator 49 to the control unit 9.

The second main passage 51 is a fuel pipe that leads the fuel, which is accumulated in the accumulator 49, to the testing apparatus body 7. A downstream end of the second main passage 51 is connected to the fuel supply passage 22, which is formed in the second block 15. Thus, the fuel is supplied to the fuel supply passage 5 of the nozzle body 1 that is placed in the body block 11.

The third main passage 52 is a fuel pipe that returns the fuel, which is discharged out of the testing apparatus body 7, to the high-pressure fuel tank 43. An upstream end of the third main passage 52 is connected to the fuel discharge passage 23, which is formed in the first block 14. Thus, the fuel, which is discharged out of the testing apparatus body 7, returns via the third main passage 52 to the high-pressure fuel tank 43.

A discharge pressure adjusting valve 57 is provided on the way of the third main passage 52. The discharge pressure adjusting valve 57 opens when a discharge pressure of the fuel discharged out of the testing apparatus body 7 is larger than a predetermined pressure, to keep the discharge pressure of the fuel discharged out of the testing apparatus body 7 at the predetermined pressure.

A second pressure sensor 58 is provided in the third main passage 52 downstream the discharge pressure adjusting valve 57. The second pressure sensor 58 detects the fuel pressure of the fuel in the third main passage 52 to be returned to the high-pressure fuel tank 43, and outputs the fuel pressure to the control unit 9.

A fuel cooler 59 is also provided in the third main passage 52 just upstream the high-pressure fuel tank 43. The fuel cooler 59 cools and liquefies the fuel to be returned to the high-pressure fuel tank 43. The fuel cooler 59 is operated in accordance with the kind of the fuel used in the endurance test.

In the first embodiment, the fuel circulation system 8 is provided with a body detour circuit 45 for bypassing the testing apparatus body 7.

The body detour circuit 45 includes a purge valve 61 and a first bypass passage 62. The purge valve 61 is connected to the accumulator 49. When the purge valve 61 opens, the first bypass passage 62 leads the fuel accumulated in the accumulator 49 to the third main passage 52 at a position downstream the discharge pressure adjusting valve 57, to bypass the testing apparatus body 7. The control unit 9 controls opening and closing operations of the purge valve 61.

In the first embodiment, the fuel circulation system 8 is further provided with a pressure return circuit 46 that pressurizes the fuel and returns the pressurized fuel to the high-pressure fuel tank 43. The pressure return circuit 46 is provided in a second bypass passage 63, which is for bypassing a part of a downstream portion of the third main passage 52. The pressure return circuit 46 includes a three-way switching valve 64, a purge tank 65, a compressor 66 and a check valve 67.

The three-way switching valve 64 is located at a branch point of the third main passage 52 and the second bypass passage 63, to switch the fuel passage, which is communicated to the high-pressure fuel tank 43, to one of the third main passage 52 and the second bypass passage 63. The control unit 9 controls the operation of the three-way switching valve 64. The purge tank 65 is a high-pressure container for accumulating vaporized fuel therein. The compressor 66 pressurizes and liquefies the vaporized fuel. The control unit 9 controls an operation of the compressor 66. When the three-way switching valve 64 is switched to the third main passage 52, the check valve 67 prevents the fuel passing through the third main passage 52 from flowing backward toward the compressor 66.

The high-pressure fuel tank 43 is a gastight container that accumulates the fuel accumulated by the compressor 66. A first safety valve 68 is provided at an upper portion in the high-pressure fuel tank 43. The first safety valve 68 opens when the pressure in the high-pressure fuel tank 43 becomes abnormally large.

Further, a second safety valve 69 is provided in the first main passage 48 in the high-pressure fuel tank 43. The second safety valve 69 opens when the fuel pressure in the first main passage 48 becomes abnormally large.

Furthermore, a third pressure sensor 71 is provided in the high-pressure fuel tank 43, to detect the fuel pressure in the high-pressure fuel tank 43. The fuel pressure detected by the third pressure sensor 71 is outputted to the control unit 9.

The control unit 9 is a microcomputer with a conventional construction including functions of: a CPU that performs respective calculation processes; a memory device such as RAM, ROM, SRAM, EEPROM that stores respective programs and data; an input circuit; an output circuit; a power source circuit; etc. The control unit 9 performs the respective calculation processes in accordance with operations inputted on an operation panel and sensor signals detected by respective sensors, and controls respective electrical functional components based on results of the calculation processes.

The driving circuit 72 supplies driving power current to the adjusting device 28 of the contact load adjuster 12 and the electric motor 31 of the contact load generator 13. The control unit 9 controls the driving circuit 72 based on the results of the calculation processes, to control the operations of the adjusting device 28 and the electric motor 31.

When a driving switch is turned on, the control unit 9 performs the respective calculation processes based on the programs stored in the ROM and the sensor signals transmitted to the RAM.

A control program, i.e., a control function, which is provided in the control unit 9, is described in the following.

The control unit 9 is provided with respective control programs to perform a main control function, a repeated contact operation stopping function, a contact load controlling function, an operation temperature controlling function, an operation pressure controlling function, a circulation passage switching function, etc, which are described in detail in the following.

The main control function is a basic control function of the endurance testing apparatus. The main control function is served by a control program that performs the respective calculation processes based on: the contact load, the contact repetition times, the fuel pressure and the fuel temperature, which are inputted into the control unit 9; their target values, proper ranges and limit ranges; and respective sensor signals, and transmits control outputs to the respective electric functional components based on the result of the calculation processes.

An example procedure of the main control function is described in the following, referring to FIG. 4.

Figure 4:
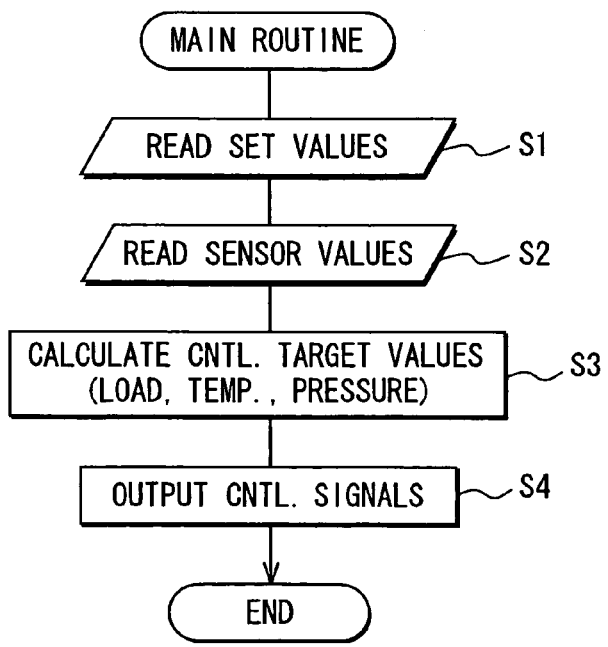
FIG. 4 is a flowchart showing an example procedure of a main control function of the endurance testing apparatus according to the first embodiment.

When the driving switch of the endurance testing apparatus is turned on to enter a main routine of the main control function, in a step represented as "START" in FIG. 4, the control unit 9 reads respective operational values of the endurance testing apparatus, which are set by the operation panel and the like, in step S1. Specifically, the control unit 9 reads: the contact repetition times, the contact load, the fuel pressure and the fuel temperature; their target values; and set values of the proper range, the limit range, etc.

Next, the control unit 9 reads the respective sensor signals in step S2.

Further, the control unit 9 performs respective calculation processes in step S3. Specifically, the control unit 9 performs the calculation processes to perform the repeated contact operation stopping function, the contact load controlling function, the operation temperature controlling function, the operation pressure controlling function, the circulation passage switching function, etc.

Furthermore, the control unit 9 transmits control outputs based on the result of the calculation processes to the respective electric functional components in step S4.

Then, the control unit 9 completes this main routine in a step represented as "END" in FIG. 4. Practically, the control unit 9 repeats the above-described main routine until the operation of the endurance testing apparatus stops.

The repeated contact operation stopping function includes a contact counting function to count contact repetition times Ni between the nozzle body 1 and the needle 2, and an automatic stopping function to stop the endurance testing apparatus automatically when the contact repetition times Ni, which is counted by the contact counting function, reaches a preset target contact repetition times Nt, which is $10^7$ times, for example.

Specifically, the repeated contact operation stopping function detects rotational frequency of the rotation shaft 33, i.e., the contact repetition times between the nozzle body 1 and the needle 2, by using the rotation sensor 41, which is provided in the contact load generator 13, and then automatically stops the endurance testing operation of the endurance testing apparatus, that is, at least an operation of the electric motor 31 in the contact load generator 13 when the counted contact repetition times Ni reaches the target contact repetition times Nt.

An example procedure of the repeated contact operation stopping function is described in the following, referring to FIG. 5.

Figure 5:
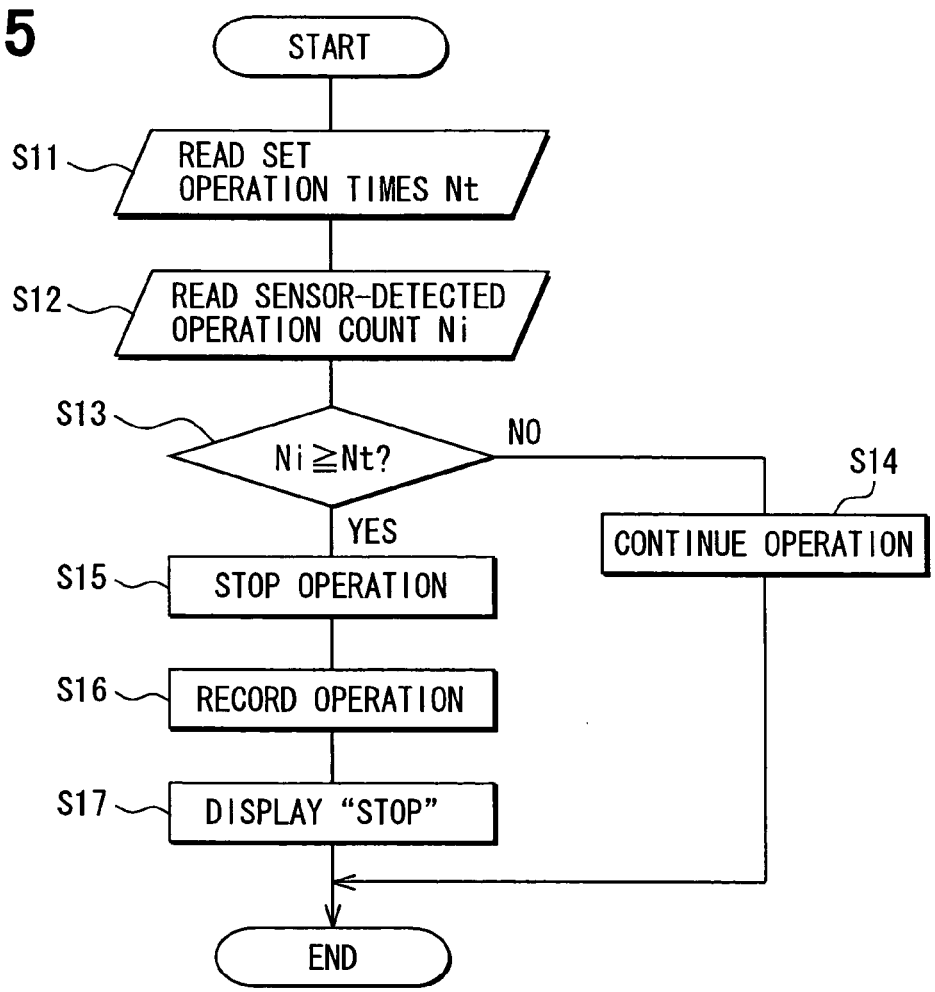
FIG. 5 is a flowchart showing an example procedure of a repeated contact operation stopping function of the endurance testing apparatus according to the first embodiment.
Figure 15:
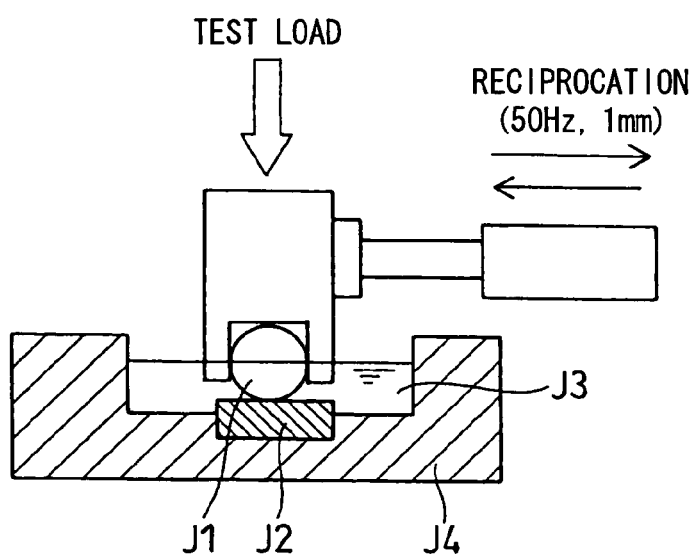
FIG. 15 is a diagram schematically showing a conventional high frequency reciprocating rig.

When the process goes into the contact repetition times controlling routine in a step represented as "START" in FIG. 5, the control unit 9 reads the target contact repetition times Nt, which is inputted on the operation panel and the like, in step S11.

Next, the control unit 9 reads the contact repetition times Ni, which is counted by the rotation sensor 41, in step S12.

Further, the control unit 9 determines whether the contact repetition times Ni has reached the target contact repetition times Nt, i.e., Ni≧Nt, or not in step S13. If No (Ni<Nt) in the step S13, the control unit 9 continues the operation of the endurance testing apparatus in step S14, and completes the contact repetition times controlling routine.

If Yes (Ni≧Nt) in the step S13, the control unit 9 automatically stops the endurance testing operation of endurance testing apparatus. Specifically, the control unit 9 stops at least the operation of the electric motor 31 in the contact load generator 13 in step S15, stores the operational state in the memory device in step S16, indicates a stop of the operation on an indication panel and the like in step S17, and completes the contact repetition times controlling routine.

Then, the nozzle assembly, which is a target of the endurance test, is taken out of the body block 11 to investigate the abrasion states of the valve seat of the nozzle body 1, the seat portion of the valve seat, and the sliding portion between the nozzle body 1 and the needle 2, to evaluate the lubrication performance of the fuel and the reliability of the nozzle assembly.

Figure 6:
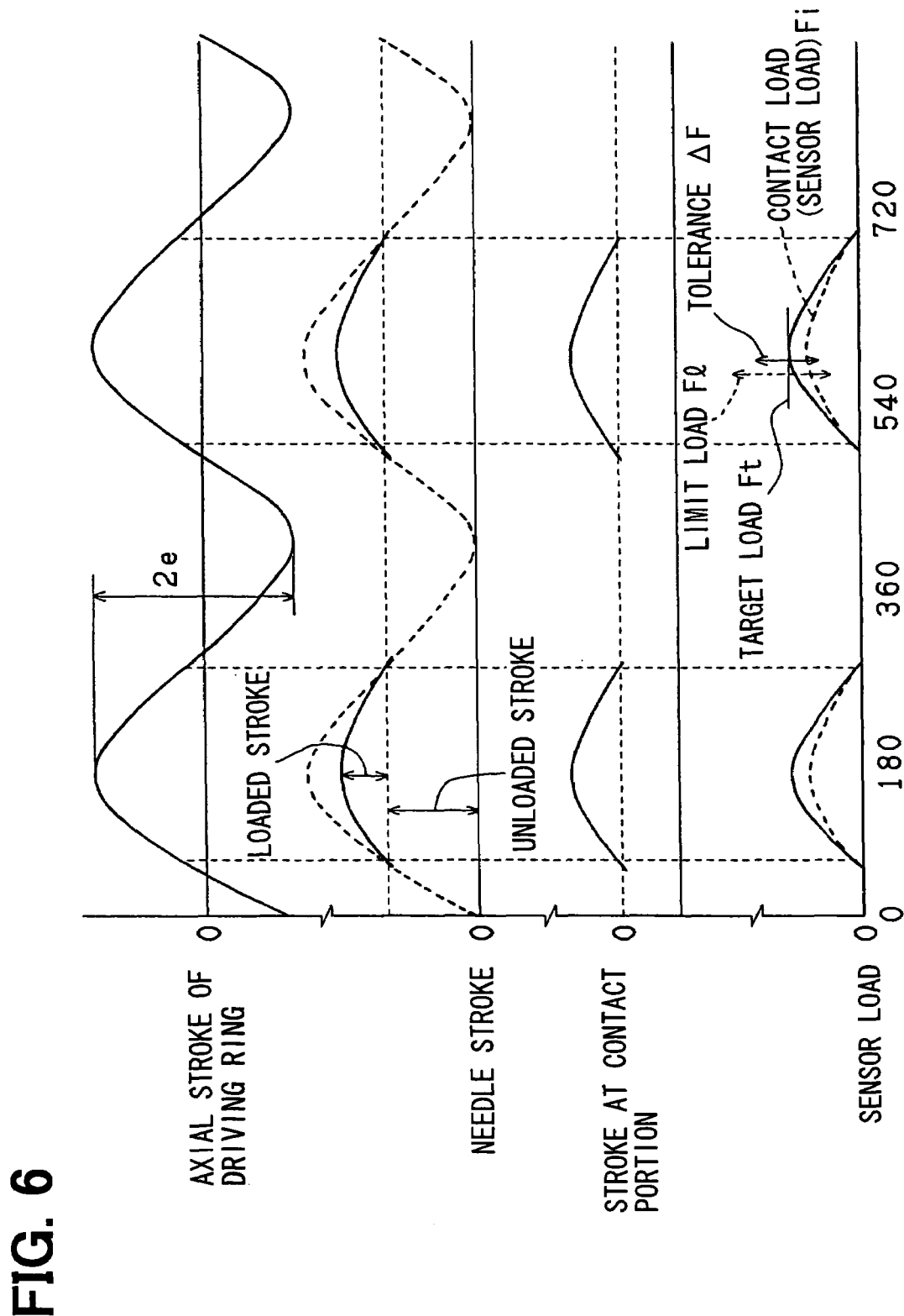
FIG. 6 is a timing chart showing actions of a test specimen relative to a rotational angle of a rotation shaft of the contact load generator of the endurance testing apparatus according to the first embodiment.

The contact load controlling function is described in the following, referring to FIG. 6. FIG. 6 is a timing chart showing the endurance test operational states, i.e., (1) an axial stroke of the driving ring 35 due to the eccentric rotation of the eccentric cam 34, (2) a stroke of the needle 2, (3) a stroke at the contact portion between the nozzle body 1 and the needle 2, and (4) a change of the contact load Fi detected by the load sensor 26, relative to the rotational angle of the rotation shaft 33.

In the first embodiment, the contact load controlling function includes a contact load adjusting function and a load-based test stopping function. The contact load adjusting function controls the contact load adjuster 12 to adjust the contact load Fi to the target load Ft when the contact load Fi, which is detected by the load sensor 26, is not within a preset proper load range, which is larger than Ft−ΔF/2 and smaller than Ft+ΔF/2 in the present embodiment, i.e., when |Ft−Fi|≧ΔF/2 in the present embodiment. The load-based test stopping function automatically stops the endurance testing operation when the contact load Fi, which is detected by the load sensor 26, is not within a preset limit load range, which is larger than Ft−Fl/2 and smaller than Ft+Fl/2 in the present embodiment, i.e., when |Ft−Fi|≧Fl/2 in the present embodiment.

In the first embodiment, the contact load adjusting function is served by a control program that calculates a moving direction and a moving amount of the sensor support block 27 to adjust the contact load Fi to the target load Ft when the contact load Fi, which is detected by the load sensor 26, is not within the preset proper load range, and drives the adjusting device 28 based on the result of the calculation.

In the first embodiment, a feedback control of the adjusting device 28 is performed to adjust the contact load Fi to the target load Ft when the contact load Fi, which is detected by the load sensor 26, is out of the preset proper load range. Alternatively, the feedback control of the adjusting device 28 may be performed to adjust the contact load Fi, which is detected by the load sensor 26, to the target load Ft at all times.

In the first embodiment, the load-based test stopping function includes not only the function to stop the endurance testing operation automatically when the contact load Fi, which is detected by the load sensor 26, gets out of the preset limit load range, but also a function to stop the endurance testing operation automatically when an adjustment number of times n, which is the time for the above-described contact load adjusting function to drive the adjusting device 28, i.e., the time when the contact load Fi gets out of the proper load range and the control unit 9 performs the feedback control of the adjusting device 28, reaches a preset upper limit times k.

An example procedure of the contact load controlling function is described in the following, referring to FIG. 7.

Figure 7:
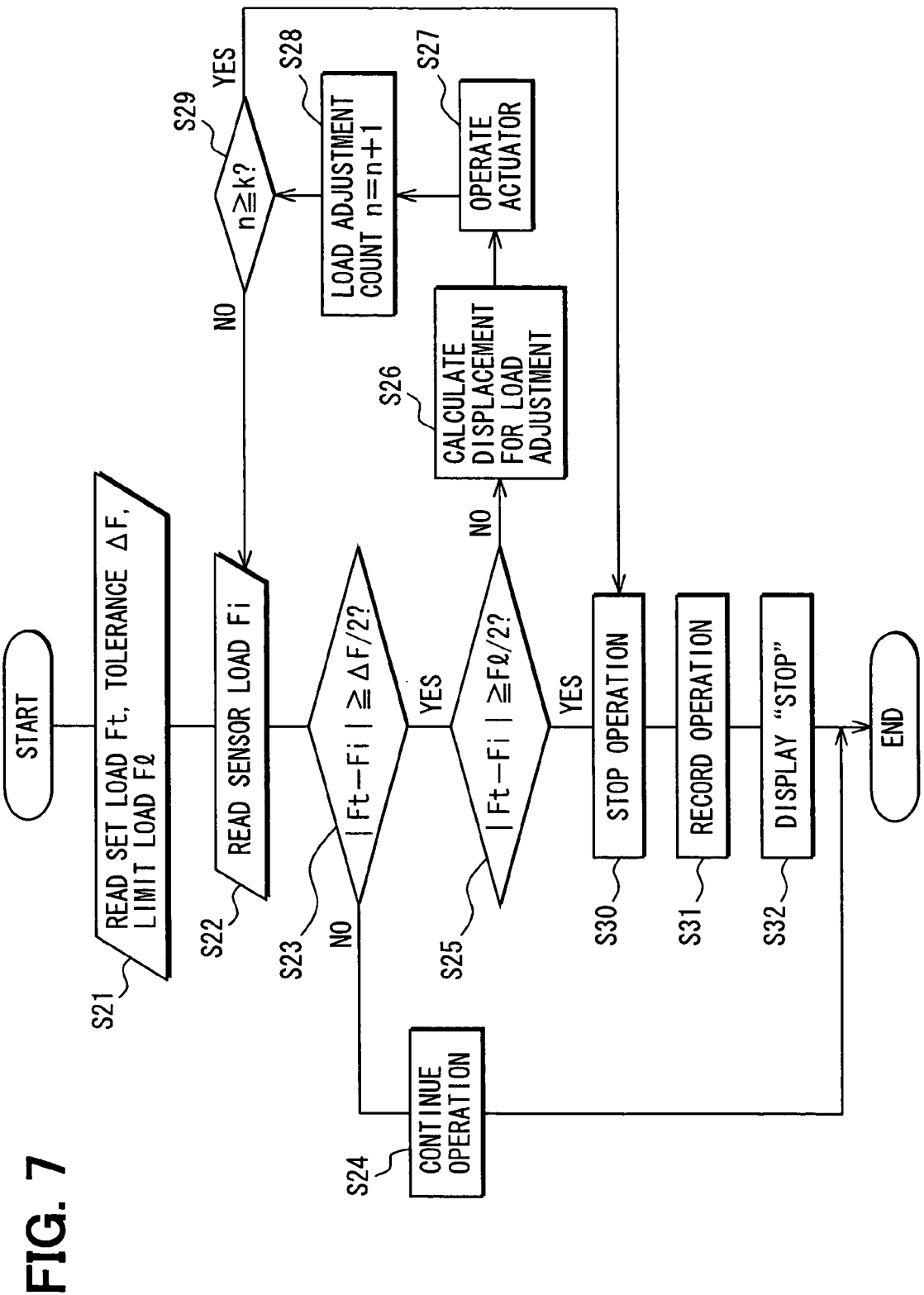
FIG. 7 is a flowchart showing an example procedure of a contact load controlling function of the endurance testing apparatus according to the first embodiment.

When the process goes into the contact load controlling routine in a step represented as "START" in FIG. 7, the control unit 9 reads the target load Ft, the proper load range ΔF, the limit load range Fl, which are inputted on the operation panel and the like, in step S21.

Next, the control unit 9 reads the contact load Fi, which is detected by the load sensor 26, in step S22.

Further, the control unit 9 determines whether the contact load Fi is out of the proper load range or not, i.e., whether |Ft−Fi|≧ΔF/2, in step S23.

If No in the step S23, the contact load Fi is within the proper load range, and the control unit 9 continues the operation of the endurance testing apparatus in step S24, and completes the contact load controlling routine.

If Yes in the step S23, i.e., if the contact load Fi is out of the proper load range, the control unit 9 determines whether the contact load Fi is out of the limit load range or not, i.e., whether |Ft−Fi|≧Fl/2 or not, in step S25.

If No in the step S25, the contact load Fi is out of the proper load range yet within the limit load range. Thus, the control unit 9 controls the contact load adjuster 12 to adjust the contact load Fi to the target load Ft, and counts one in the adjustment number of times n.

That is, the control unit 9 calculates a moving direction and a moving amount of the sensor support block 27 to adjust the contact load Fi to the target load Ft in step S26, drives the adjusting device 28 based on the calculation result to adjust the contact load Fi in step S27, and counts one in the adjustment number of times n in step S28.

Next, the control unit 9 determines whether the adjustment number of times n has reached a preset upper limit times k, i.e., n≧k or not in step S29.

If No in the step S29, the adjustment number of times n has not reached the upper limit times k. Thus, the process goes back to the step S22 to continue the operation of the endurance testing apparatus.

If Yes in the step S25, i.e., if the contact load Fi is out of the limit load range, or if Yes in the step S29, i.e., if the adjustment number of times n has reached the upper limit times k, the control unit 9 automatically stops the endurance testing operation by the endurance testing apparatus. Specifically, the control unit 9 stops at least an operation of the electric motor 31 in the contact load generator 13 in step S30, stores the driving state in the memory device in step S31, indicates the stop of the operation on the indication panel and the like in step S32, and completes the contact load controlling routine.

The operation temperature controlling function includes a temperature adjusting function and a temperature-based test stopping function. The temperature adjusting function controls the temperature adjusting device 53 to adjust the sensor temperature Ti to the target temperature Tt when the sensor temperature Ti, which is detected by the first temperature sensor 25, gets out of a preset proper temperature range. In the first embodiment, the temperature adjusting function operates when the sensor temperature Ti increases to Tt+ΔT/2 or larger, or decreases to Tt−ΔT/2 or smaller, i.e., when |Tt−Ti|≧ΔT/2. The temperature-based test stopping function automatically stops the endurance testing operation when the sensor temperature Ti, which is detected by the first temperature sensor 25, gets out of a preset limit temperature range. In the first embodiment, the temperature-based test stopping function operates when the sensor temperature Ti increases to Tt+Tl/2 or larger, or decreases to Tt−Tl/2 or smaller, i.e., when |Tt−Ti|≧Tl/2.

In the first embodiment, the temperature adjusting function is served by a control program that calculates a positive or negative heat amount to adjust the sensor temperature Ti to the target temperature Tt when the sensor temperature Ti, which is detected by the first temperature sensor 25, is not within the preset proper temperature range, and controls the temperature adjusting device 53 based on the result of the calculation.

In the first embodiment, a feedback control of the temperature adjusting device 53 is performed to adjust the sensor temperature Ti to the target temperature Tt when the sensor temperature Ti, which is detected by the first temperature sensor 25, is out of the preset proper temperature range. Alternatively, the feedback control of the temperature adjusting device 53 may be performed to adjust the sensor temperature Ti, which is detected by the first temperature sensor 25, to the target temperature Tt at all times.

In the first embodiment, the temperature-based test stopping function includes not only the function to stop the endurance testing operation automatically when the sensor temperature Ti, which is detected by the first temperature sensor 25, gets out of the preset limit temperature range, but also a function to stop the endurance testing operation automatically when an adjustment number of times n, which is the time for the above-described temperature adjusting function to control the temperature adjusting device 53, i.e., the time when the sensor temperature Ti gets out of the proper temperature range and the control unit 9 performs the feedback control of the temperature adjusting device 53, reaches a preset upper limit times k.

An example procedure of the operation temperature controlling function is described in the following, referring to FIG. 8.

Figure 8:
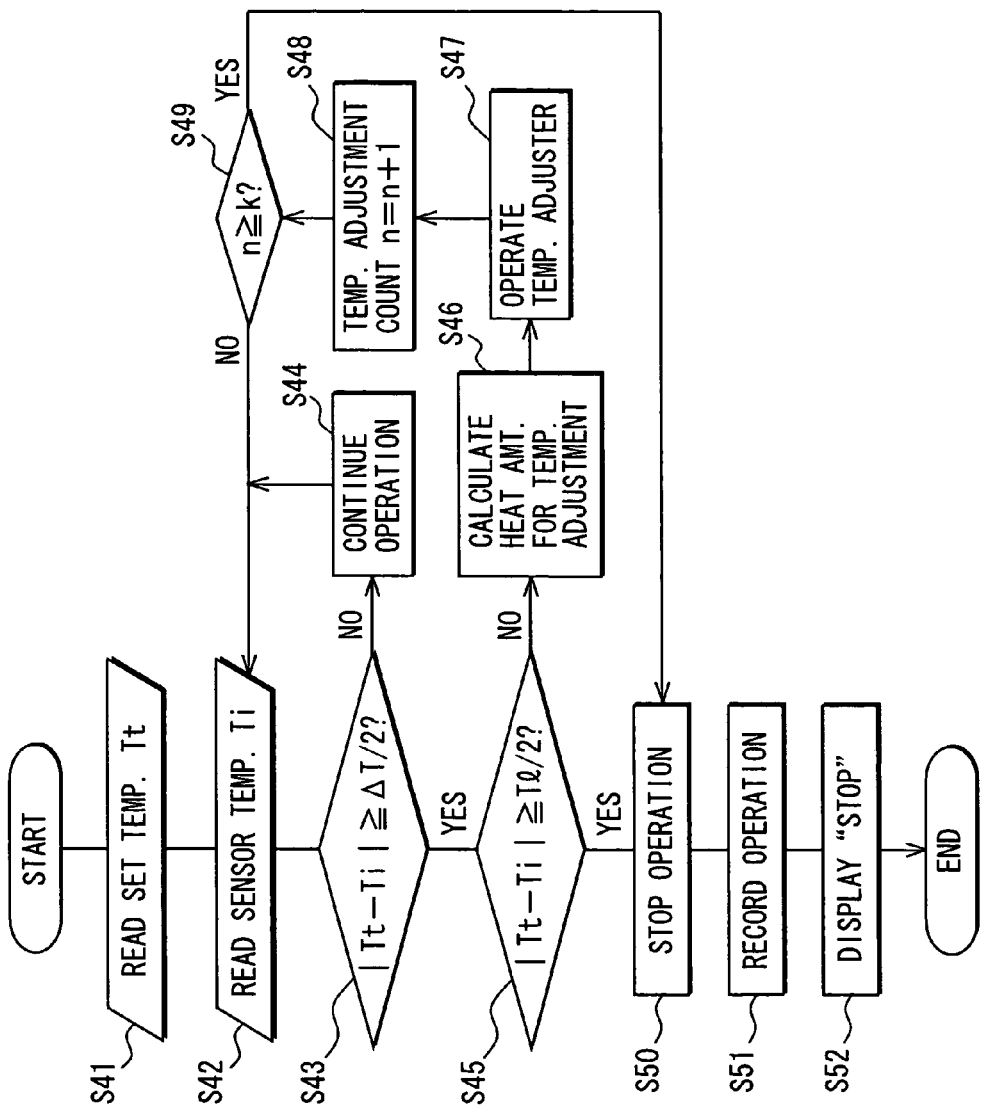
FIG. 8 is a flowchart showing an example procedure of operation temperature controlling function of the endurance testing apparatus according to the first embodiment.

When the process goes into the operation temperature controlling routine in a step represented as "START" in FIG. 8, the control unit 9 reads the target temperature Tt, the temperature tolerance ΔT and the limit temperature range Tl, which are set by using the operation panel and the like, in step S41.

Next, the control unit 9 reads the sensor temperature Ti, which is detected by the first temperature sensor 25, in step S42.

Further, the control unit 9 determines whether the sensor temperature Ti is out of the proper temperature range, i.e., |Tt−Ti|≧ΔT/2 or not in step S43.

If No in the step S43, the sensor temperature Ti is within the proper temperature range. Thus, the control unit 9 continues the operation of the endurance testing apparatus in step S44, and the process goes back to the step S42.

If Yes in the step S43, i.e., if the sensor temperature Ti is out of the proper temperature range, the control unit 9 determines whether the sensor temperature Ti is out of the limit temperature range, i.e., whether |Tt−Ti|≧Tl/2 or not in step S45.

If No in the step S45, the sensor temperature Ti is out of the proper temperature range yet within the limit temperature range. Thus, the control unit 9 controls the temperature adjusting device 53 to adjust the sensor temperature Ti to the target temperature Tt, and counts one in the adjustment number of times n.

That is, the control unit 9 calculates the heat amount to adjust the sensor temperature Ti to the target temperature Tt in step S46, controls the temperature adjusting device 53 to adjust the sensor temperature Ti based on the calculation result in the step S46 in step S47, and counts one in the adjustment number of times n in step S48.

Next, the control unit 9 determines whether the adjustment number of times n has reached a preset upper limit times k, i.e., n≧k or not in step S49.

If No in the step S49, the adjustment number of times n has not reached the upper limit times k. Thus, the process goes back to the step S42 to continue the operation of the endurance testing apparatus.

If Yes in the step S45, i.e., if the sensor temperature Ti is out of the limit temperature range, or if Yes in the step S49, i.e., if the adjustment number of times n has reached the upper limit times k, the control unit 9 automatically stops the endurance testing operation by the endurance testing apparatus. Specifically, the control unit 9 stops at least the operation of the electric motor 31 in the contact load generator 13 in step S50, stores the operational state in the memory device in step S51, indicates a stop of the operation on the indication panel and the like in step S52, and completes the operation temperature controlling routine.

The operation pressure controlling function includes a pressure adjusting function and a pressure-based test stopping function. The pressure adjusting function controls a discharge amount out of the high-pressure pump 47 per unit time to adjust the sensor pressure Pi to the target pressure Pt when the sensor pressure Pi, which is detected by the first pressure sensor 55, gets out of a preset proper pressure range. In the first embodiment, the pressure adjusting function operates when the sensor pressure Pi increases to Pt+ΔP/2 or larger, or decreases to Pt−ΔP/2 or smaller, i.e., when |Pt−Pi|≧ΔP/2. The pressure-based test stopping function automatically stops the endurance testing operation when the sensor pressure Pi, which is detected by the first pressure sensor 55, gets out of a preset limit pressure range. In the first embodiment, the pressure-based test stopping function operates when the sensor pressure Pi increases to Pt+Pl/2 or larger, or decreases to Pt−Pl/2 or smaller, i.e., when |Pt−Pi|≧Pl/2.

In the first embodiment, the pressure adjusting function is served by a control program that calculates the discharge amount of fuel to adjust the sensor pressure Pi to the target pressure Pt when the sensor pressure Pi, which is detected by the first pressure sensor 55, is not within the preset proper load range, and controls the high-pressure pump 47 based on the result of the calculation.

In the first embodiment, a feedback control of the high-pressure pump 47 is performed to adjust the sensor pressure Pi to the target pressure Pt when the sensor pressure Pi, which is detected by the first pressure sensor 55, is out of the preset proper pressure range. Alternatively, the feedback control of the high-pressure pump 47 may be performed to adjust the sensor pressure Pi, which is detected by the first pressure sensor 55, to the target pressure Pt at all times.

In the first embodiment, the pressure-based test stopping function includes not only the function to stop the endurance testing operation automatically when the sensor pressure Pi, which is detected by the first pressure sensor 55, gets out of the preset limit pressure range, but also a function to stop the endurance testing operation automatically when an adjustment number of times n, which is the time for the above-described pressure adjusting function to control the high-pressure pump 47, i.e., the time when the sensor pressure Pi gets out of the proper pressure range and the control unit 9 performs the feedback control of the high-pressure pump 47, reaches a preset upper limit times k.

An example procedure of the operation pressure controlling function is described in the following, referring to FIG. 9.

Figure 9:
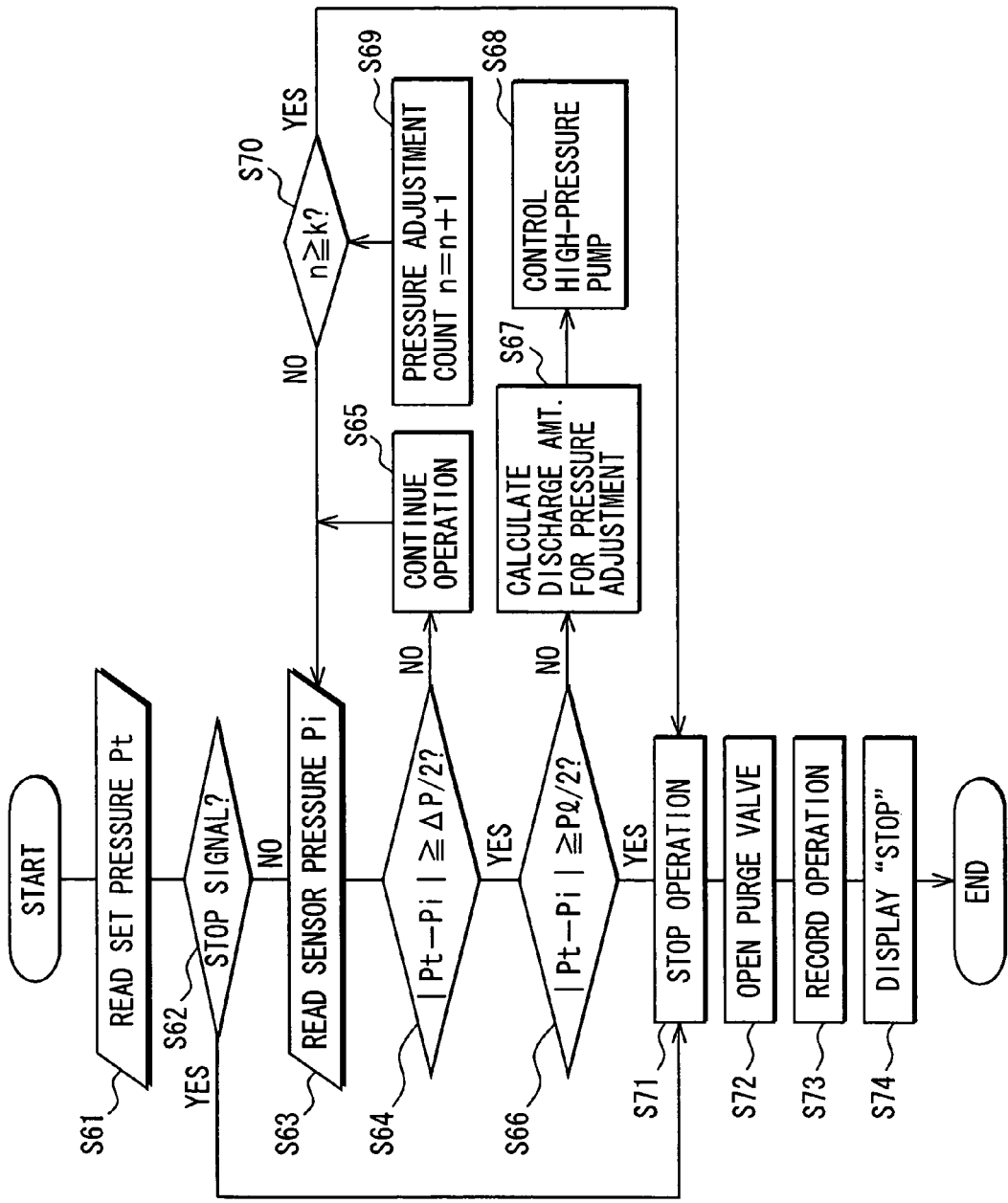
FIG. 9 is a flowchart showing an example procedure of an operation pressure controlling function of the endurance testing apparatus according to the first embodiment.

When the process goes into the operation pressure controlling routine in a step represented as "START" in FIG. 9, the control unit 9 reads the target pressure Pt, the pressure tolerance ΔP and the limit pressure range Pi, which are set by using the operation panel and the like, in step S61.

Next, the control unit 9 determines whether an operation stopping signal is inputted or not in step S62.

If No in the step S62, i.e., if the driving switch is turned on in the step S62, the control unit 9 reads the sensor pressure Pi, which is detected by the first pressure sensor 55, in step S63.

Further, the control unit 9 determines whether the sensor pressure Pi is out of the proper pressure range, i.e., whether |Pt−Pi|≧ΔP/2 or not in step S64.

If No in the step S64, the sensor pressure Pi is within the proper pressure range. Thus, the control unit 9 continues the operation of the endurance testing apparatus in step S65, and the process goes back to the step S63.

If Yes in the step S64, i.e., if the sensor pressure Pi is out of the proper pressure range, the control unit 9 determines whether the sensor pressure Pi is out of the limit pressure range, i.e., whether |Pt−Pi|≧Pl/2, or not in step S66.

If No in the step S66, the sensor pressure Pi is out of the proper pressure range yet within the limit pressure range. Thus, the control unit 9 controls the temperature adjusting device high-pressure pump 47 to adjust the sensor pressure Pi to the target pressure Pt, and counts one in the adjustment number of times n.

That is, the control unit 9 calculates the discharge amount of fuel to adjust the sensor pressure Pi to the target pressure Pt in step S67, controls the high-pressure pump 47 to adjust the sensor pressure Pi based on the calculation result in the step S67 in step S68, and counts one in the adjustment number of times n in step S69.

Next, the control unit 9 determines whether the adjustment number of times n has reached a preset upper limit times k, i.e., n≧k or not in step S70.

If No in the step S70, the adjustment number of times n has not reached the upper limit times k. Thus, the process goes back to the step S63 to continue the operation of the endurance testing apparatus.

If Yes in the step S62, i.e., if the control unit 9 has received an operation stopping command, if Yes in the step S66, i.e., if the sensor pressure Pi is out of the limit pressure range, or if Yes in the step S70, i.e., if the adjustment number of times n has reached the upper limit times k, the control unit 9 automatically stops the endurance testing operation by the endurance testing apparatus. Specifically, the control unit 9 stops at least the operation of the electric motor 31 in the contact load generator 13 in step S71, opens the purge valve 61 in step S72, stores the operational state in the memory device in step S73, indicates a stop of the operation on the indication panel and the like in step S74, and completes the operation pressure controlling routine.

The circulation passage switching function is served by a program that performs switching controls and operations of the main circulation circuit 44, the body detour circuit 45 and the pressure return circuit 46 of the fuel circulation system 8. Specifically, (1) when a return fuel pressure Prt in the third main passage 52, which is detected by the second pressure sensor 58, is larger than a tank pressure Ptank in the high-pressure fuel tank 43, which is detected by the third pressure sensor 71, i.e., when Ptank<Prt, the program circulates the fuel in the main circulation circuit 44; (2) when the return fuel pressure Prt in the third main passage 52, which is detected by the second pressure sensor 58, is not larger than the tank pressure Ptank in the high-pressure fuel tank 43, which is detected by the third pressure sensor 71, i.e., when Ptank≧Prt, the program circulates the fuel via the pressure return circuit 46, pressurizes the fuel in the pressure return circuit 46 and returns the fuel to the high-pressure fuel tank 43; and (3) when the control unit 9 receives an operation stopping command in the endurance testing operation, the program returns the fuel accumulated in the accumulator 49 via the body detour circuit 45 to the high-pressure fuel tank 43.

An example procedure of the circulation passage switching function is described in the following, referring to FIG. 10.

Figure 10:
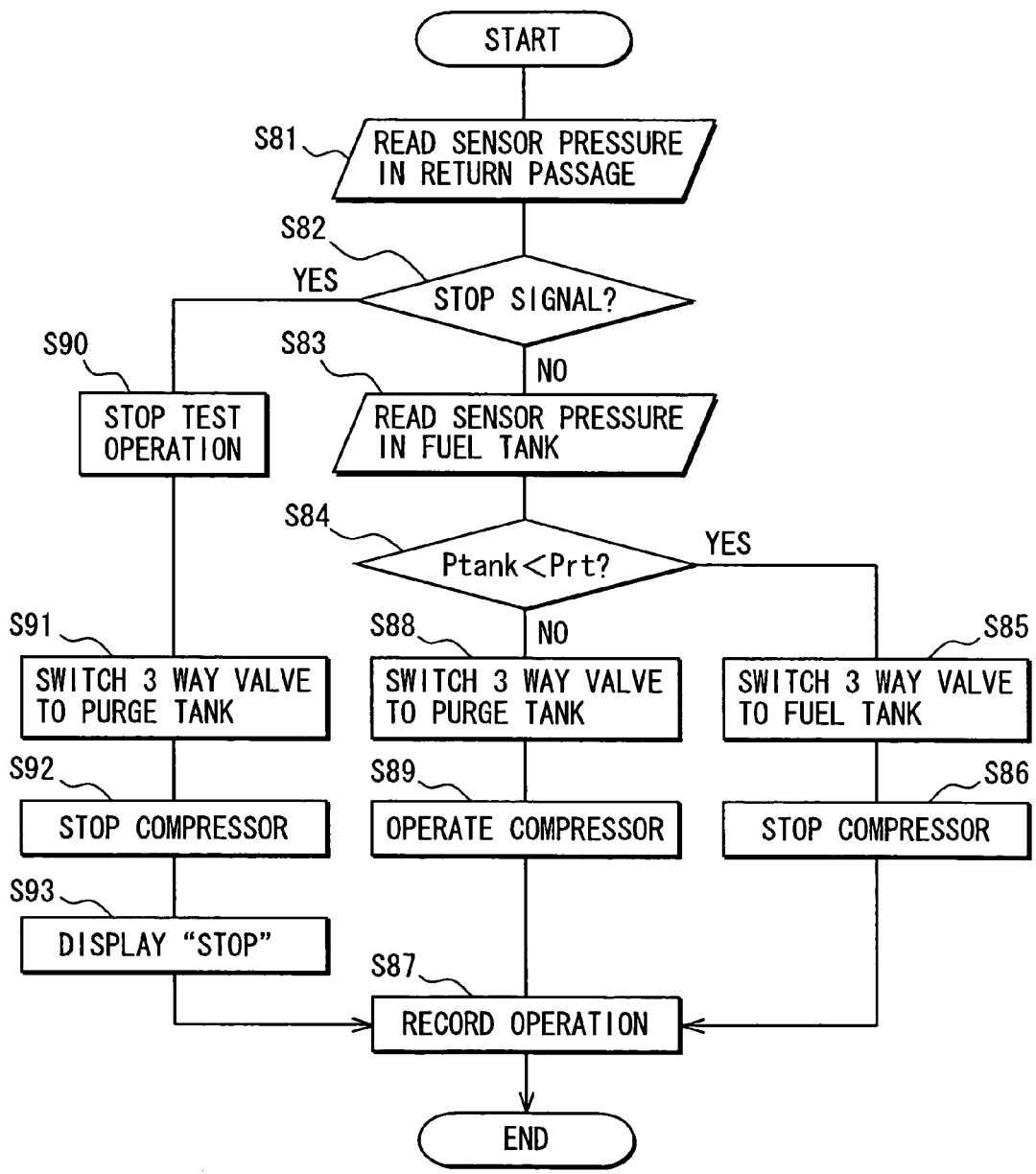
FIG. 10 is a flowchart showing an example procedure of a circulation passage switching function of the endurance testing apparatus according to the first embodiment.

When the process goes into the circulation passage switching control routine in a step represented as "START" in FIG. 10, the control unit 9 reads the return fuel pressure Prt, which is detected by the second pressure sensor 58, in step S81.

Next, the control unit 9 determines whether an operation stopping signal is inputted or not in step S82.

If No in the step S82, i.e., if the driving switch is turned on in the step S82, the control unit 9 reads the tank pressure Ptank, which is detected by the third pressure sensor 71, in step S83.

Further, the control unit 9 determines whether the return fuel pressure Prt is larger than the tank pressure Ptank, i.e., whether Ptank<Prt or not in step S84.

If Yes in the step S84, i.e., if Ptank<Prt in the step S84, the control unit 9 circulates the fuel in the main circulation circuit 44. That is, the control unit 9 switches the three-way switching valve 64 to communicate the fuel passage, which is communicated to the high-pressure fuel tank 43, with the third main passage 52 and to block the second bypass passage 63 in step S85. Next, if the compressor 66 is in operation, the control unit 9 stops the compressor 66 in step S86, stores the operational state in the memory device in step S87, and completes the circulation passage switching control routine.

If No in the step S84, i.e., if Ptank≧Prt in the step S84, the control unit 9 circulates the fuel in the pressure return circuit 46. That is, the control unit 9 switches the three-way switching valve 64 to communicate the fuel passage, which is communicated to the high-pressure fuel tank 43, with the second bypass passage 63 in step S88. Next, the control unit 9 operates the compressor 66 to pressurize the vaporized fuel in step S89, and then stores the operational state in the memory device in step S87, and completes the circulation passage switching control routine.

If Yes in the step S82, i.e., if the control unit 9 has received the operation stopping command, the control unit 9 circulates the fuel in the body detour circuit 45. That is, the control unit 9 stops the endurance testing operation by the endurance testing apparatus in step S90, opens the purge valve 61 in step S91, stops the compressor 66 if the compressor 66 is in operation in step S92, indicates a stop of the operation on the indication panel and the like in step S93, stores the operational state in the memory device in the step S87, and completes the circulation passage switching control routine pressure controlling routine.

The above-described construction of the endurance testing apparatus according to the first embodiment serves the following effects.

(1) The nozzle assembly is placed in the body block 11 of the testing apparatus body 7, and the nozzle body 1 and the needle 2 repeats contacting with and separating from each other in the state that the contacting/separating portion A of the nozzle body 1 and the needle 2 is exposed to the fuel. Thus, it is possible to perform an endurance test of the nozzle assembly, which is difficult to perform by using high frequency reciprocating ring (HFRR).

(2) The contact load generator 13, which includes the electric motor 31 and the rotation-reciprocation converter 32, reciprocates the needle 2. Thus, it is possible to repeat the contacting and separating operations of the nozzle body 1 and the needle 2, without using an actual internal combustion engine and the like as in the conventional testing apparatus. That is, it is possible to increase the speed for the nozzle body 1 and the needle 2 to repeat contacting with and separating from each other easily, just by increasing the rotational speed of the electric motor 31. As a result, it is possible to decrease a testing time of the endurance test.

(3) The contact load generator 13, which includes the electric motor 31 and the rotation-reciprocation converter 32, reciprocates the needle 2. Thus, it is possible to repeat contacting and separating operations between the nozzle body 1 and the needle 2 without using an actual internal combustion engine and the like as in the conventional testing apparatus. Thus, it is possible to decrease a cost of the endurance testing apparatus, and to reduce the size and weight of the endurance testing apparatus.

(4) The fuel circulation system 8 passes the fuel through the contacting/separating portion A between the nozzle body 1 and the needle 2, so that the abrasion powder does not accumulate at the contacting/separating portion A. Thus, it is possible to prevent the abrasion powder, which is accumulated at the contacting/separating portion A, from varying the abrasion amount to cause a malfunction of low accuracy of endurance evaluation.

(5) The fuel circulation system 8 includes the closed loop that supplies the fuel passed through the contacting/separating portion A between the nozzle body 1 and the needle 2, again to the contacting/separating portion A, so that the endurance testing apparatus do not waste the fuel. Further, it is possible to prevent the fuel from leaking into the atmosphere, to secure high safety performance.

(6) The fuel circulation system 8 supplies the fuel to the contacting/separating portion A of the nozzle body 1 and the needle 2, so that it is possible to perform the endurance test by adopting low critical fuel, which is easily vaporized, for the fuel passing through the contacting/separating portion A of the nozzle body 1 and the needle 2.

(7) The repeated contact operation stopping function, which is served by the control unit 9, automatically stops the endurance testing operation when the contact repetition times Ni between the nozzle body 1 and the needle 2 contact operation time has reached the preset target contact repetition times Nt. Thus, the contact repetition times Ni does not vary test by test, and it is possible to improve the accuracy of the endurance evaluation by the endurance testing apparatus.

(8) The contact load controlling function, which is served by the control unit 9, drives the adjusting device 28 of the contact load adjuster 12 to adjust the contact load Fi to the target load Ft when the contact load Fi, which is detected by the load sensor 26, gets out of the preset proper load range. Thus, it is possible to prevent the factors of abrasion development, etc. from causing a malfunction of large change of the contact load Fi. Accordingly, it is possible to improve the accuracy of the endurance testing apparatus.

(9) The load-based test stopping function, which is served by the control unit 9, automatically stops the endurance testing operation when the contact load Fi, which is detected by the load sensor 26, gets out of the preset limit load range. Thus, the endurance testing apparatus immediately stops when a malfunction such as a breakage of the nozzle assembly, which is the test specimen, a seizure of the nozzle assembly, etc. in the endurance testing operation. Accordingly, it is possible to examine breakage state, abrasion state at the time of breakage, and seizure state of the nozzle assembly in detail.

(10) The operation temperature controlling function, which is served by the control unit 9, controls the temperature adjusting device 53 to adjust the sensor temperature Ti to the target temperature Tt when the sensor temperature Ti, which is detected by the first temperature sensor 25, gets out of the preset proper temperature range. Thus, it is possible to prevent the endurance evaluation from varying due to the temperature change of the contacting/separating portion A, to improve the accuracy of the endurance evaluation.

Second Embodiment

Figure 11:
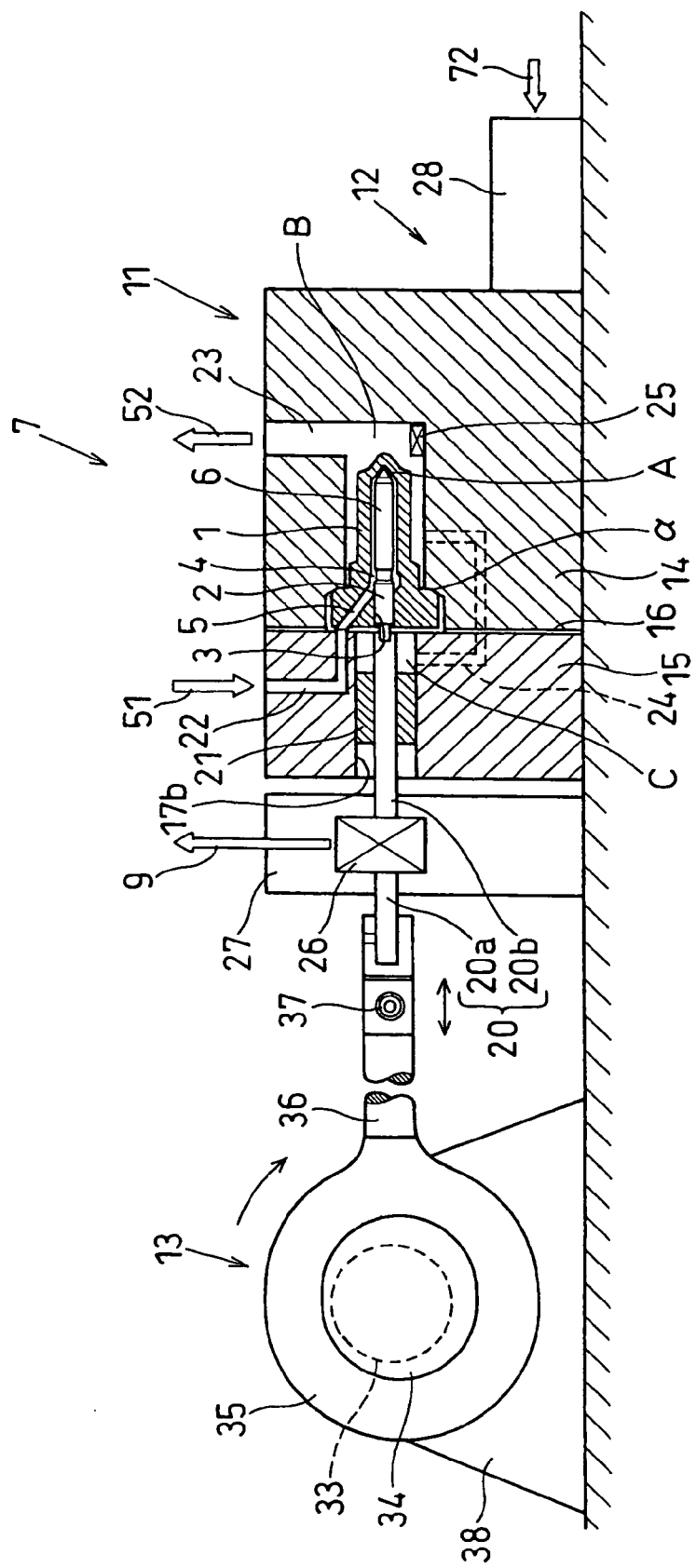
FIG. 11 is a schematic cross-sectional view showing a principal portion of an endurance testing apparatus according to a second embodiment of the present invention.

An endurance testing apparatus according to the second embodiment is described in the following, referring to FIG. 11. In the following embodiments, the referential numerals assigned as same as in the first embodiment substantially represents the components that have functions substantially the same as those in the first embodiment. In the following embodiments, the differences from the first embodiment are described.

In the above-described first embodiment, the contact load Fi between the nozzle body 1 and the needle 2 is detected by the load sensor 26 interposed between the load shaft 18, which is in contact with the leading end of the nozzle body 1 and the sensor support block 27. The adjusting device 28 moves the sensor support block 27 in the axial direction to adjust the contact load Fi between the nozzle body 1 and the needle 2.

In the second embodiment, the load sensor 26 is located on the way of the drive shaft 20, which is for reciprocating the needle 2, to detect the contact load Fi between the nozzle body 1 and the needle 2 by using the load acting onto the drive shaft 20. The adjusting device 28 moves the body block 11 in the axial direction to adjust the contact load Fi between the nozzle body 1 and the needle 2.

Specifically, the drive shaft 20 is divided into a first and second drive shafts 20a, 20b in the axial direction. The first and second drive shafts 20a, 20b sandwiches the load sensor 26, which is installed in the sensor support block 27, therebetween.

Further, the axial clearance a between the nozzle body 1 and the first block 14 is set to zero, i.e., $\alpha$=0, so that the body block 11 receives the load generated in the nozzle body 1. Thus, it is possible to adjust the contact load Fi between the nozzle body 1 and the needle 2, i.e., the contact load Fi detected by the load sensor 26, by moving the body block 11 by the adjusting device 28 in the axial direction.

The above-described construction of the endurance testing apparatus according to the second embodiment serves the following effects.

(1) The load sensor 26 can directly detect the load acting on the needle 2. Thus, it is possible to improve an accuracy of the endurance evaluation.

(2) The load shaft 18, which is mentioned in the first embodiment, is not necessary. Thus, it is possible to decrease an axial length of the testing apparatus body 7.

(3) By eliminating the load shaft 18 mentioned in the first embodiment, a seal between the load shaft 18 and the first block 14 is neither necessary. Thus, it is possible to securely prevent the fuel from leaking.

Third Embodiment

Figure 12:
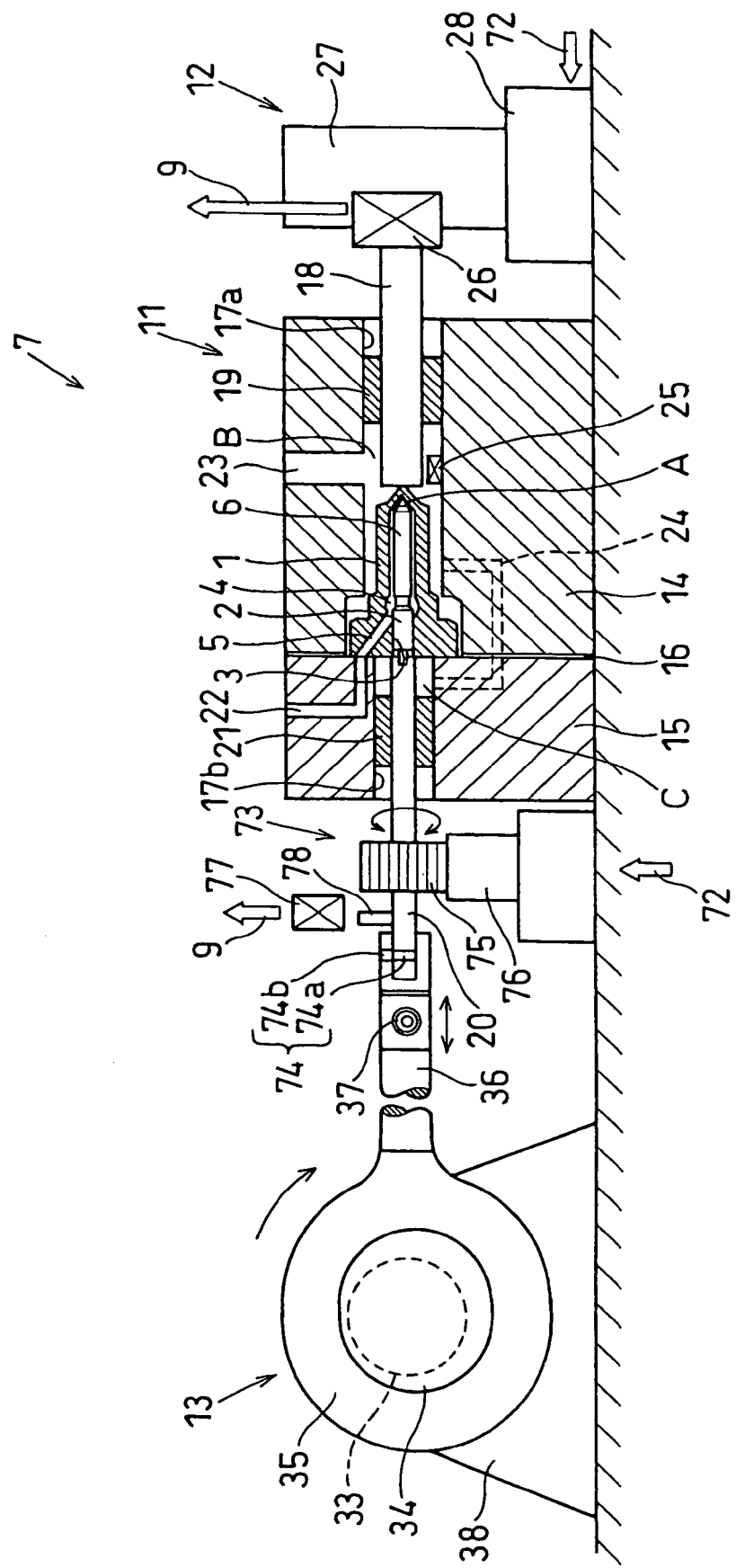
FIG. 12 is a schematic cross-sectional view showing a principal portion of an endurance testing apparatus according to a third embodiment of the present invention.

An endurance testing apparatus according to the third embodiment is described in the following, referring to FIG. 12.

In the above-described first embodiment, the contact load generator 13 of the testing apparatus body 7 reciprocates the needle 2 in the axial direction.

In the third embodiment, the testing apparatus body 7 is provided with a rotating means 73, which rotates the needle 2 relative to the needle body 1, in addition to the contact load generator 13.

That is, in the third embodiment, the testing apparatus body 7 can rotate the needle 2 by the rotating means 73 in reciprocating the needle 2 by the contact load generator 13 in the axial direction.

In the third embodiment, the rotating means 73 rotates the drive shaft 20 in combination with the contact load generator 13. In the third embodiment, the drive shaft 20 is rotatably installed. Specifically, in the third embodiment, a second joint 74 is provided between the drive shaft 20 and the joint 37 to allow the rotation of the drive shaft 20 and to transmit only an axial displacement of the joint 37 to the drive shaft 20. An example of the second joint 74 is described in the following. The second joint 74 is provided with an annular groove 74a that is formed on over an outer circumference of the drive shaft 20 and a pin 74b that is engaged with the annular groove 74a in a member connected to the joint 37. The drive shaft 20 can rotate relative to the joint 37.

In the rotating means 73, a second electric motor 76 rotationally drives a gear wheel 75, which is fixed on a circumference of the drive shaft 20. The control unit 9 controls a rotational speed of the second electric motor 76 via the driving circuit 72.

An engaging range between the gear wheel 75 and the second electric motor 76 extends large in the axial direction, so that the second electric motor 76 can rotationally drive the gear wheel 75 even when the gear wheel 75 reciprocates together with the drive shaft 20. The drive shaft 20 and the gear wheel 75 may be coupled with each other at a press-fitting portion in which a relative sliding movement between the drive shaft 20 and the gear wheel 75 is allowed in the axial direction and a relative rotation between the drive shaft 20 and the gear wheel 75 is restricted.

The gear wheel 75 is an example of the rotating means. Alternatively, other rotation transmitting means such as belt may be adopted as the rotating means. Further, the rotation of the electric motor 31, which is used in the contact load generator 13, may be used also for rotationally driving the drive shaft 20. In this case, it is an option to provide an individually variable rotation transmission means that changes the rotational speed of the drive shaft 20 relative to the rotational speed of the electric motor 31, or to provide a rotation transmission interrupting means that interrupts a transmission of the rotation of the electric motor 31 to the drive shaft 20.

The contact load generator 13 is provided with the second rotation sensor 77 that detects the rotation of the drive shaft 20, to detect the rotational speed of the needle 2 relative to the nozzle body 1. Specifically, the second rotation sensor 77 in the third embodiment is served by a pickup sensor that detects a rotational state of the drive shaft 20, by a second pulser 78, which is a magnetic body and the like fixed on the drive shaft 20, coming closer to and apart from the second rotation sensor 77.

The rotational state of the drive shaft 20, which is detected by the second rotation sensor 77, i.e., the rotational state of the needle 2 is outputted to the control unit 9.

The control unit 9 controls the rotational speed of the second electric motor 76 to adjust the rotational speed of the drive shaft 20, which is detected by the second rotation sensor 77, to the target rotational speed, which is preset by using a control panel and the like.

In the endurance testing apparatus according to the third embodiment, the needle 2 is rotatably installed relative to the needle body 1, which is fixedly supported, so that the endurance testing apparatus can simulate the operation of the fuel injection valve in which the needle 2 rotates relative to the nozzle body 1 while the nozzle body 1 and the needle 2 repeats contacting with and separating from each other. In this manner, the endurance testing apparatus can perform the endurance test in an operational condition close to an actual one, so that it is possible to improve the accuracy of the endurance evaluation.

Fourth Embodiment

Figure 13:
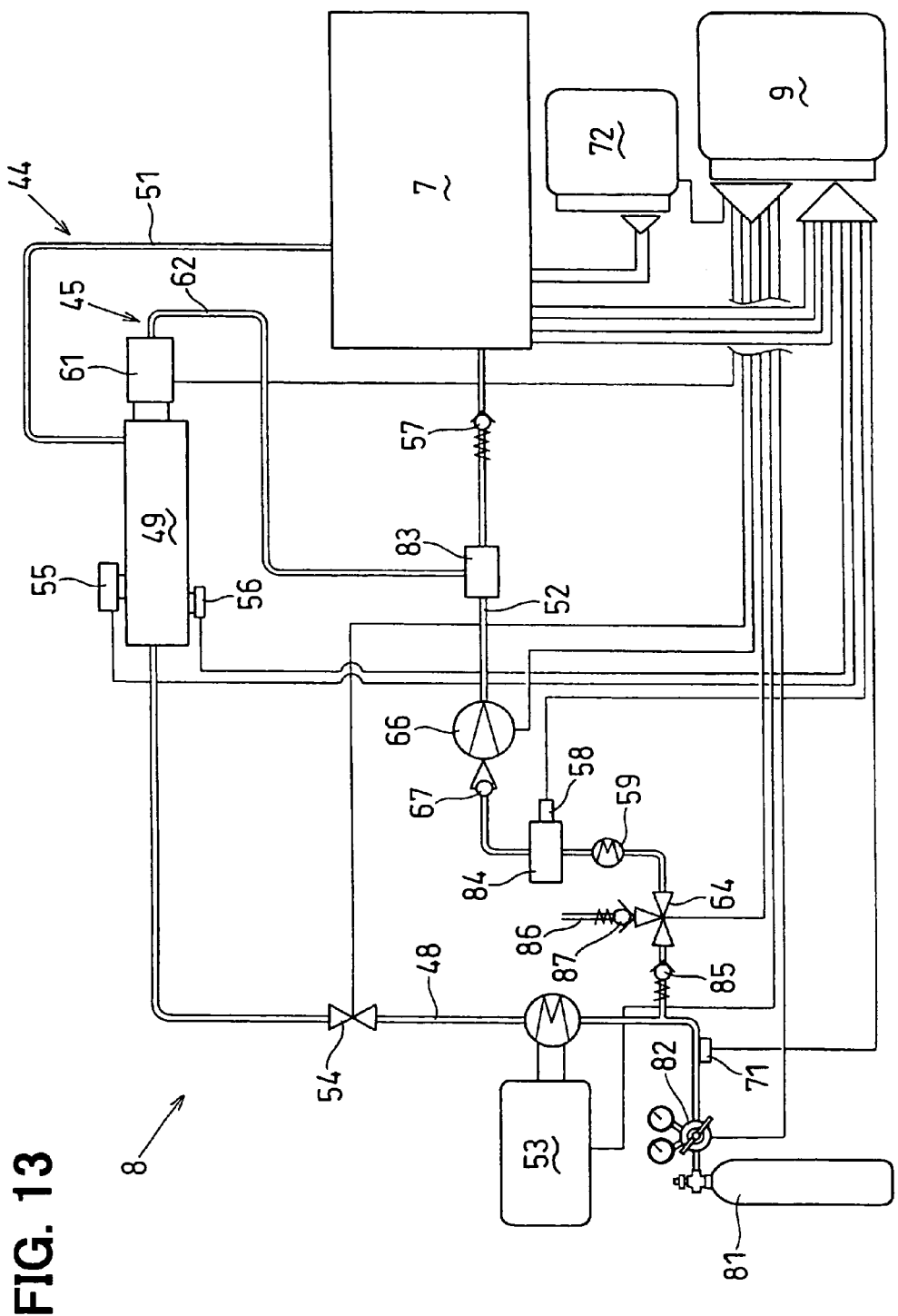
FIG. 13 is a schematic cross-sectional view showing a principal portion of an endurance testing apparatus according to a fourth embodiment of the present invention.

An endurance testing apparatus according to the fourth embodiment is described in the following, referring to FIG. 13.

In the above-described first to third embodiments, the endurance testing apparatus uses low critical fuel as the testing medium fluid.

In the fourth embodiment, the endurance testing apparatus performs the endurance test by using gaseous fuel such as hydrogen fuel, which is easily volatilized at normal temperature and at normal pressure as the testing medium fluid.

A part of the construction of the fuel circulation system 8 in the fourth embodiment is different from that in the first embodiment, and is described in the following.

In the fourth embodiment, a high-pressure cylinder 81, which accumulates the gaseous fuel in pressurized state, serves as fuel supply source instead of the high-pressure fuel tank 43 in the first embodiment. A pressure adjusting/cutoff valve 82 is provided at an outlet portion of the high-pressure cylinder 81, to adjust an opening/closing degree of the high-pressure cylinder 81 and the fuel discharge pressure out of the high-pressure cylinder 81.

In the fourth embodiment, the third pressure sensor 71, which is described also in the first embodiment, is configured to detect the fuel supply pressure at an upstream side position in the first main passage 48.

The control unit 9 is provided with a pressure adjusting function, which automatically controls an opening degree of the pressure adjusting/cutoff valve 82 in the endurance testing operation, to adjust the fuel supply pressure, which is detected by the third pressure sensor 71, to a preset target pressure.

In the fourth embodiment, the return fuel, which returns to the first main passage 48 after passing through the testing apparatus body 7 or the body detour circuit 45, is a gas, and has a pressure smaller than the pressure in the high-pressure cylinder 81. Thus, the fuel, which has passed through the testing apparatus body 7 or the body detour circuit 45, is pressurized by the compressor 66 at all times, and then returns to the first main passage 48.

Specifically, the gaseous fuel, which has passed through the testing apparatus body 7 or the body detour circuit 45, flows via the first purge tank 83, the compressor 66, the check valve 67, the second purge tank 84, the fuel cooler 59, the three-way switching valve 64 and the second check valve 85 to the first main passage 48 at a position between the high-pressure cylinder 81 and the temperature adjusting device 53.

In the fourth embodiment, the three-way switching valve 64 is located between the second purge tank 84 and the upstream side position of the first main passage 48, to switch the gaseous fuel, which has passes through the second purge tank 84, to one of the upstream side of the first main passage 48 and the release passage 86. The release passage 86 is provided with a safety valve 87 that opens to releases the gaseous fuel to the atmosphere when the return pressure increases to a predetermined pressure.

In the fourth embodiment, the second pressure sensor 58, which is described also in the first embodiment, is configured to detect an inner pressure in the second purge tank 84, i.e., the return pressure. The third pressure sensor 71, as mentioned above, detects the fuel supply pressure at the upstream side position in the first main passage 48.

The control unit 9 is provided with a switching control function, which opens the three-way switching valve 64 to communicate the third main passage 52 with the first main passage 48 to return the gaseous fuel, which is accumulated in the second purge tank 84, to the upstream side position of the first main passage 48 when the return pressure, which is detected by the second pressure sensor 58, becomes larger than the fuel supply pressure, which is detected by the third pressure sensor 71.

The control unit 9 is further provided with an automatic valve closing function, which closes all of the cutoff valve 54, the pressure adjusting/cutoff valve 82 and the three-way switching valve 64 when the endurance testing operation stops.

Accordingly, when the endurance testing operation stops, the gaseous fuel, the pressure of which is larger than the predetermined valve opening pressure of the safety valve 87, such gaseous fuel as hydrogen that is harmless in terms of safety, is released out of the release passage 86 to the atmosphere. The safety valve 87 also serves a function to maintain a predetermined residual pressure in the fuel circulation system 8, in addition to a function to counteract a rapid pressure release.

In the fourth embodiment, an example to release a harmless part of the gaseous fuel to the atmosphere is described. Alternatively, the gaseous fuel out of the release passage 86 may be collected in another tank. By this configuration to collect the gaseous fuel to the another tank, it becomes possible to perform the endurance test with harmful gaseous fuel in a safe manner.

Fifth embodiment

Figure 14:
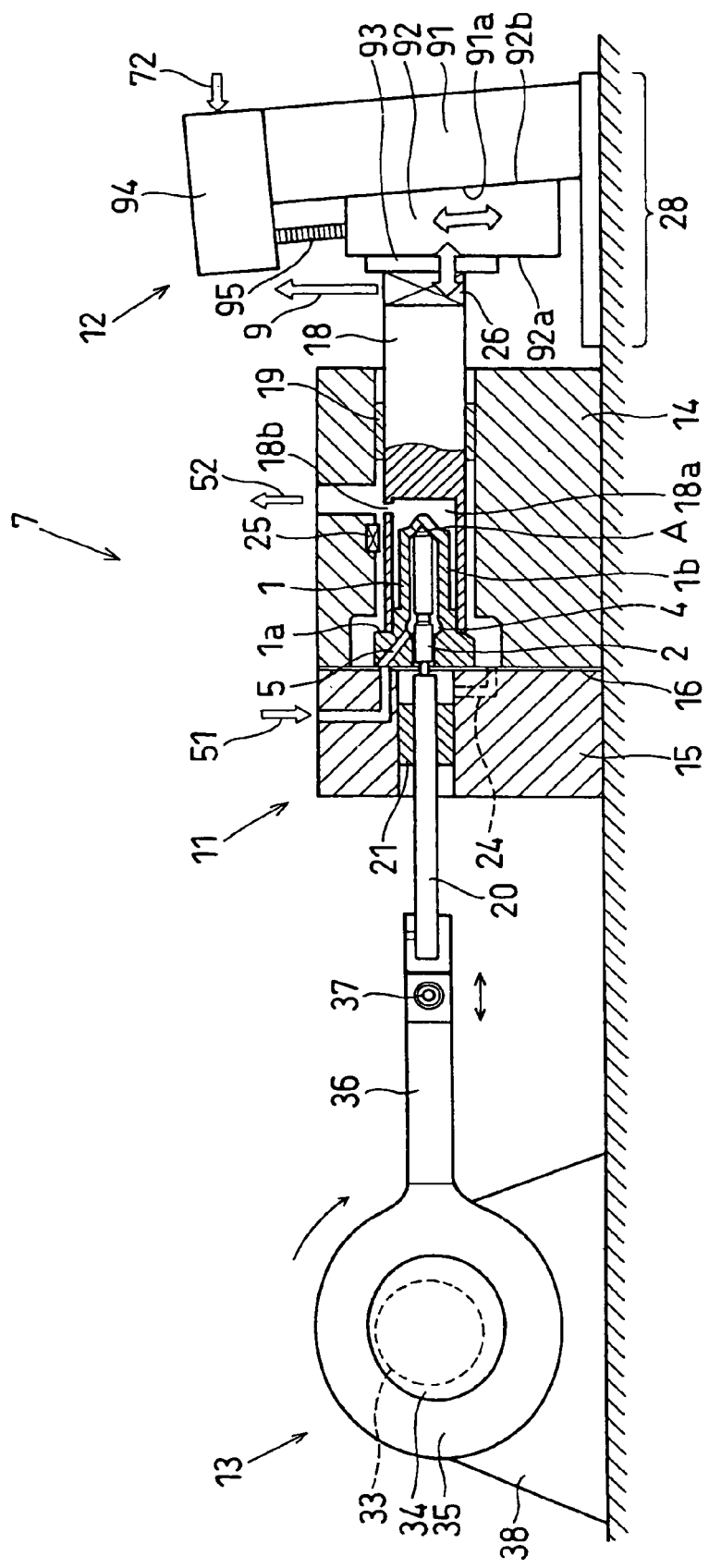
FIG. 14 is a schematic cross-sectional view showing a principal portion of an endurance testing apparatus according to a fifth embodiment of the present invention.

An endurance testing apparatus according to the fifth embodiment is described in the following, referring to FIG. 14. The endurance testing apparatus according to the fifth embodiment has a construction, which is different mainly in (1) the adjusting device 28 and in (2) a contact position of the load shaft 18 and the nozzle body 1 from that according to the first embodiment.

In the first embodiment, as shown in FIG. 1, the adjusting device 28 directly moves the sensor support block 27 along the axial direction of the load shaft 18 by a driving means (not shown) installed in the adjusting device 28, to adjust the contact load between the nozzle body 1 and the needle 2. In the fifth embodiment, as shown in FIG. 14, the adjusting device 28 moves a tapered table 92 along a slant face 91a, which is slightly inclined to a fictive plane, which is perpendicular to the axial direction of the load shaft 18, to adjust the contact load between the nozzle body 1 and the needle 2.

Specifically, the adjusting device 28 in the fifth embodiment includes a slant base 91, the tapered table 92, a slider 93 and a driving means. The slant base 91 has the above-mentioned slant face 91a that is slightly inclined to the fictive plane, which is perpendicular to the axial direction of the load shaft 18. The tapered table 92 is installed to slide on the slant face 91a. The slider 93 is interposed between the tapered table 92 and the load sensor 26 to reduce the friction therebetween. The driving means moves tapered table 92 along the slant face 91a.

The driving means includes an electric motor 94, which rotates when energized, and a rotation/linear displacement converter, which coverts the rotation of the electric motor 94 into a linear displacement. The rotation/linear displacement converter includes a male screw 95, which is rotationally driven by the electric motor 94, and a female screw (not shown), which is formed in the tapered table 92 to be screw-fastened to the male screw 95. The rotation of the electric motor 94 rotates the male screw 95 to move the tapered table 92 upward or downward along the slant face 91a.

The tapered table 92 has a vertical face 92a and a tapered face 92b. The vertical face 92a is perpendicular to the load shaft 18, and in sliding contact with the slider 93. The tapered face 92b is slightly inclined to the vertical face 92a and in parallel with the slant face 91a of the slant base 91. The axial load of the load shaft 18, i.e., the contact load between the nozzle body 1 and the needle 2, is adjusted by the moving height of tapered table 92 along the slant face 91a.

By using the above-described the adjusting device 28, it is possible to move the load shaft 18 quite minutely relative to the moving height of the tapered table 92 along the slant face 91a of the slant base 91. Accordingly, it is possible to adjust the axial load of the load shaft 18, i.e., the contact load between the nozzle body 1 and the needle 2 with a high degree of accuracy. It is also possible to decrease a driving torque of the electric motor 94 in the adjusting device 28.

In the first embodiment, the load shaft 18 is in contact with the leading end of the nozzle body 1. In the fifth embodiment, the left end (in the drawing) of the load shaft 18 is in contact with the shoulder portion 1a of the nozzle body 1, to apply the contact load to the nozzle body 1 via the shoulder portion 1a.

The load shaft 18 in the fifth embodiment is provided with a hollow 18a at a left side portion (in the drawing) thereof, to install the leading end side portion of the nozzle body 1, i.e., the stem portion 1b therein, forming a clearance between the circumferential face of nozzle body 1 and an inner circumferential face of the hollow 18a. The load shaft 18 is further provided with a communication hole 18b to lead the fuel, which has injected out of the injection hole of the nozzle body 1 into the hollow 18a, to the third main passage 52.

By applying the contact load onto the shoulder portion 1a of the nozzle body 1 as in the fifth embodiment, the loading condition applied to the nozzle assembly, i.e., the loading position of the nozzle assembly is approximately the same as that of the nozzle assembly in an actual usage condition, i.e., the nozzle assembly used in an actual vehicle. Accordingly, it becomes possible to perform the endurance test of the abrasions at the valve seat of the nozzle body 1, the seat portion of the needle 2 and the sliding portion of the nozzle body 1 and the needle 2 in a condition close to the actual usage condition. That is, it is possible to evaluate the reliabilities of the lubrication performance of the fuel and the nozzle assembly in the condition close to the actual one.

MODIFIED EMBODIMENTS

The target load Ft, which is constant in each of the above-described embodiments, may be changed in a stepped manner or in a continuous manner, in accordance with the contact repetition times Ni, the elapsed time of the endurance test, etc. The target temperature Tt, which is constant in each of the above-described embodiments, may be changed in a stepped manner or in a continuous manner, in accordance with the contact repetition times Ni, the elapsed time of the endurance test, etc. Likewise, the target pressure Pt, which is constant in each of the above-described embodiments, may be changed in a stepped manner or in a continuous manner, in accordance with the contact repetition times Ni, the elapsed time of the endurance test, etc.

In each of the above-described embodiments, the axial direction of the reciprocation of the contact load generator 13 is aligned with the axial direction of the needle 2. Alternatively, the axial direction of the reciprocation of the contact load generator 13 may be different from the axial direction of the needle 2, by using a coupler that transmits the reciprocation of the contact load generator 13 to the needle 2.

In each of the above-described embodiments, the contact load generator 13 is formed from the electric motor 31 and the rotation-reciprocation converter 32. Alternatively, other kind of driving devices such as a linear solenoid, a piezoelectric actuator, etc. can reciprocate the needle 2 in its axial direction instead of the contact load generator 13.

In each of the above-described embodiments, the nozzle assembly, which is formed from the nozzle body 1 and the needle 2, is described as an example of the test specimen. The endurance testing apparatus according to the present invention is also applicable to the endurance test of various valve device such as: the valve devices in the fuel injection system including an electromagnetic valve of a fuel injection valve, an adjusting valve of a fuel pump, a pressure-reducing valve, etc.; other valve devices for vehicle including an EGR valve, air intake valve etc.; and valve devices for home uses or commercial uses. That is, the endurance testing apparatus according to the present invention can generally perform the endurance test of the valve device or other kinds of device than the valve device in which two members repeat contacting with and separated from each other.

This description of the invention is merely exemplary in nature and, thus, variations that do not depart from the gist of the invention are intended to be within the scope of the invention. Such variations are not to be regarded as a departure from the spirit and scope of the invention.

What is claimed is:

1. An endurance testing apparatus for performing endurance testing of a contacting/separating portion in which a first member and a second member repeatedly contact with and separate from each other, the endurance testing apparatus comprising:
    a contact load generator that, during endurance testing, repeatedly generates a contact load acting between the first member and the second member by repeatedly causing the first member and the second member to separate and then contact with each other at a contacting/separation portion by reciprocating the second member in an axial direction with respect to the first member during an endurance testing period; and
    a testing medium fluid supply means that supplies a testing medium fluid to the contacting/separating portion to expose the first member and the second member to the testing medium fluid;
    a contact load adjuster that adjusts the contact load;
    a load sensor that directly detects the contact load acting between the first member and the second member; and
    a control unit that uses feedback from the load sensor to control the contact load adjuster to continuously adjust the contact load detected by the load sensor to a predetermined target load or within a predetermined proper load range.

2. The endurance testing apparatus according to claim 1, wherein the testing medium fluid supply means passes the testing medium fluid through the contacting/separating portion.

3. The endurance testing apparatus according to claim 2, wherein the testing medium fluid supply means has a closed loop that supplies testing medium fluid passed through the contacting/separating portion again to the contacting/separating portion.

4. The endurance testing apparatus according to claim 3, wherein the closed loop supplies testing medium fluid that is volatile liquid or gas in a normal temperature and normal pressure.

5. The endurance testing apparatus according to claim 1, further comprising:
    a contact counter that counts a number of times that the first member contacts with the second member; and
    a control unit that automatically stops endurance testing when the number of times counted by the contact counter reaches a predetermined target number of times.

6. The endurance testing apparatus according to claim 1, further comprising:
    a load sensor that detects the contact load acting between the first member and the second member; and
    a control unit that automatically stops endurance testing when the contact load detected by the load sensor gets out of a predetermined limit load range.

7. The endurance testing apparatus according to claim 2, further comprising:
    a temperature adjuster that adjusts a temperature of the testing medium fluid to be supplied to the contacting/separating portion;
    a first temperature sensor that detects the temperature of the testing medium fluid at the contacting/separating portion; and
    a control unit that controls the temperature adjuster to adjust the temperature detected by the first temperature sensor to a predetermined target temperature or within a predetermined proper temperature range.

8. The endurance testing apparatus according to claim 1, further comprising a rotating means that rotates the second member relative to the first member about a center axis thereof.

9. The endurance testing apparatus according to claim 1, wherein:
    the first member is a valve body of a valve device; and
    the second member is a valve element of the valve device that repeatedly seats on and lifts off a valve seat of the valve body.

10. An endurance testing method for performing endurance testing of a contacting/separating portion in which a first member and a second member repeatedly contact with and separate from each other, the endurance testing method comprising:
    during an endurance test, repeatedly generating a contact load acting between the first member and the second member by repeatedly causing the first member and the second member to separate and then contact with each other at a contacting/separation period by reciprocating the second member in an axial direction with respect to the first member during an endurance testing period; and
    supplying a testing medium fluid to the contacting/separating portion to expose the first member and the second member to the testing medium fluid;
    adjusting the contact load;
    detecting the contact load acting between the first member and the second member; and controlling the contact load adjustment to continuously adjust the detected contact load to a predetermined target load or within a predetermined proper load range.

11. The method of claim 10 wherein the testing medium fluid is passed through the contacting/separating portion.

12. The method of claim 11 wherein a closed loop supplies testing medium fluid passing through the contacting/separating portion again to the contacting/separating portion.

13. The method of claim 12 wherein the closed loop supplies testing medium fluid that is volatile liquid or gas in a normal temperature and normal pressure.

14. The method of claim 11 further comprising:
counting a number of times that the first member contacts with the second member; and
automatically stopping endurance testing when the counted number of times reaches a predetermined target number of times.

15. The method of claim 10 further comprising:
detecting the contact load acting between the first member and the second member; and
automatically stopping endurance testing when the detected contact load gets out of a predetermined limit load range.

16. The method of claim 11 further comprising:
adjusting a temperature of the testing medium fluid to be supplied to the contacting/separating portion;
detecting the temperature of the testing medium fluid at the contacting/separating portion; and
controlling the temperature adjustment to a predetermined target temperature or within a predetermined proper temperature range.

17. The method of claim 10 further comprising rotating the second member relative to the first member about a center axis thereof.

18. The method of claim 10 wherein:
the first member is a valve body of a valve device; and
the second member is a valve element of the valve device that repeatedly seats on and lifts off a valve seat of the valve body.

* * * * *